United States Patent
McCoy et al.

(10) Patent No.: US 10,758,465 B2
(45) Date of Patent: Sep. 1, 2020

(54) SYNEPHRINE COMPOSITIONS

(71) Applicant: Follea International, Irvine, CA (US)

(72) Inventors: John McCoy, Irvine, CA (US); Ofer A. Goren, Irvine, CA (US)

(73) Assignee: Follea International, Irvine, CA (US)

( * ) Notice: Subject to any disclaimer, the term of this patent is extended or adjusted under 35 U.S.C. 154(b) by 62 days.

(21) Appl. No.: 16/036,185

(22) Filed: Jul. 16, 2018

(65) Prior Publication Data

US 2019/0110968 A1    Apr. 18, 2019

Related U.S. Application Data

(63) Continuation of application No. PCT/US2018/034375, filed on May 24, 2018.

(60) Provisional application No. 62/555,271, filed on Sep. 7, 2017, provisional application No. 62/510,499, filed on May 24, 2017.

(51) Int. Cl.

| A61K 8/34 | (2006.01) |
|---|---|
| A61K 8/37 | (2006.01) |
| A61Q 5/00 | (2006.01) |
| A61Q 7/00 | (2006.01) |
| A61K 36/752 | (2006.01) |
| A61K 8/41 | (2006.01) |
| A23L 2/52 | (2006.01) |
| A61K 31/137 | (2006.01) |
| A61K 8/23 | (2006.01) |
| A61K 8/42 | (2006.01) |
| A61K 8/44 | (2006.01) |
| A61K 8/49 | (2006.01) |
| A61K 8/97 | (2017.01) |
| A61Q 5/02 | (2006.01) |

(52) U.S. Cl.
CPC ............... *A61K 8/347* (2013.01); *A23L 2/52* (2013.01); *A61K 8/23* (2013.01); *A61K 8/345* (2013.01); *A61K 8/375* (2013.01); *A61K 8/41* (2013.01); *A61K 8/42* (2013.01); *A61K 8/44* (2013.01); *A61K 8/4926* (2013.01); *A61K 8/97* (2013.01); *A61K 31/137* (2013.01); *A61K 36/752* (2013.01); *A61Q 5/00* (2013.01); *A61Q 5/02* (2013.01); *A61Q 7/00* (2013.01); *A61K 2800/524* (2013.01); *A61K 2800/88* (2013.01)

(58) Field of Classification Search
None
See application file for complete search history.

(56) References Cited

U.S. PATENT DOCUMENTS

| 6,197,317 | B1 | 3/2001 | Klein |
| 8,048,920 | B2 | 11/2011 | Joerger et al. |
| 9,186,310 | B2 | 11/2015 | Kulesza |
| 2005/0250944 | A1* | 11/2005 | Chen ................ C07C 67/14 544/170 |
| 2006/0018975 | A1* | 1/2006 | Talbott ............. A61K 31/375 424/646 |
| 2008/0107679 | A1 | 5/2008 | Dilallo |
| 2009/0165812 | A1 | 7/2009 | Resnick et al. |
| 2016/0058723 | A1* | 3/2016 | Lee ................ A61K 31/195 424/62 |
| 2016/0256484 | A1 | 9/2016 | Doxey et al. |
| 2016/0375079 | A1 | 12/2016 | Roh et al. |
| 2017/0027856 | A1* | 2/2017 | Florence ............. A61K 8/99 |
| 2017/0135988 | A1 | 5/2017 | Goren et al. |

FOREIGN PATENT DOCUMENTS

| CN | 103271831 B | 3/2015 |
| JP | 2001019607 A | 1/2001 |
| WO | 2015172801 A1 | 11/2015 |
| WO | 2016060564 A8 | 4/2016 |

OTHER PUBLICATIONS

International Search Report and Written Opinion for PCT/US2018/034375 filed May 24, 2018, dated Aug. 21, 2018.
Extended European Search Report for Application No. 18738186.8 dated Jan. 8, 2020.

* cited by examiner

*Primary Examiner* — Robert A Wax
*Assistant Examiner* — Randeep Singh
(74) *Attorney, Agent, or Firm* — Buchanan Ingersoll & Rooney PC

(57) ABSTRACT

Disclosed herein are compositions of synephrine and a penetration enhancer and methods of reducing hair loss from pulling by applying the compositions. In one embodiment, the composition is a prewash composition comprising water, synephrine, and PEG-6 caprylic/capric glycerides.

17 Claims, 4 Drawing Sheets

| PLACEBO (Hairs) | Formula 01 (Hairs) | Reduction in Hairs (%) |
|---|---|---|
| 18 | 7 | 61% |
| 43 | 33 | 23% |
| 21 | 5 | 76% |
| 46 | 19 | 59% |
| 39 | 39 | 0% |
| 34 | 12 | 65% |
| 47 | 22 | 53% |
| 20 | 9 | 55% |
| 24 | 18 | 25% |
| 7 | 2 | 71% |
| 7 | 4 | 43% |
| 15 | 10 | 33% |
| 14 | 6 | 57% |
| 13 | 9 | 31% |
| | | |
| | Average Reduction | 44% |
| | % Responders | 93% |

Environmental Storage Specifications:

Incubator Temp (± 2): 25°C ☐  40°C ☒  50°C ☐  Other ____ °C ☐    Relative Humidity (± 5): 60% RH ☐  65% RH ☐  75% RH ☒  Other ____ % RH ☐

| TEST | Time 0 | 1 MONTH | 2 MONTHS |
|---|---|---|---|
| Product: | | | |
| Appearance/Color | Clear liquid / Light Yellow | Clear liquid / Light Yellow | Clear liquid / Light Yellow |
| Odor | Characteristics | Characteristics | Characteristics |
| pH @ 25°C | 4.03 | 3.46 | 3.35 |
| Specific Gravity @ 25°C | 1.11 | 1.11 | 1.11 |
| Package Compatibility | Match Standard | Match Standard | Match Standard |

| Analytical Assay Testing: | Results Initial:<br>Accession # 170509-0028 | 1 MONTH<br>Accession # 170609-0079 | 2 MONTHS<br>Accession # 170710-0061 |
|---|---|---|---|
| *Synephrine HCL* | *36.7%* | *38.5%* | *35.1%* |

FIG. 3

| Micro Testing | Time 0 | 1 MONTH Accession # 505545 | 2 MONTHS Accession # 513778 |
|---|---|---|---|
| Total Plate Count (TPC) | <10 cfu/g | <10 cfu/g | <10 cfu/g |
| Yeast/Mold | <10 cfu/g | <10 cfu/g | <10 cfu/g |
| Enrichment (Pathogens) | Absent | Absent | Absent |
| Pseudomonas | Absent | Absent | Absent |
| S. aureus | Absent | Absent | Absent |
| E. coli | Absent | Absent | Absent |
| Coliforms | Absent | Absent | Absent |
| Salmonella/Shigella | Absent | Absent | Absent |

FIG. 4

SYNEPHRINE COMPOSITIONS

CROSS-REFERENCE TO RELATED APPLICATIONS

This application is a continuation of and claims priority to International Application PCT/US2018/034375, filed on May 24, 2018, which is related to and claims priority to U.S. Provisional Application No. 62/555,271, filed Sep. 7, 2017, and U.S. Provisional Application No. 62/510,499 filed May 24, 2017, each of which is incorporated herein by reference by its entirety.

TECHNICAL FIELD

The present invention relates to aqueous compositions of synephrine, such as without limitation synephrine obtained from bitter orange extract and synephrine HCl, for topical application. The compositions may be used for preventing or reducing hair loss during procedures that pull at the hair.

BACKGROUND

Many hair care products and hair styling techniques require pulling on the hair and therefore exert force on the hair follicle. Often this results in hair loss. It is an object of the present invention to reduce hair loss and mitigate the damage to hair caused from procedures that pull at the hair by applying a composition of synephrine topically at hair follicles in the scalp or skin.

Many cosmetic procedures used in hair salons and at home involve exerting strong force on the hair to pull it in a direction away from the scalp. For example, washing, brushing and combing hair involves exertion of a force on the hair that pulls the hair away and out of the hair follicle. Brushing hair with vigorous, powerful strokes damages it. Such procedures result in hair shedding or hair loss. It is desirable to minimize hair breakage during hair care and styling procedures. The hair then may be treated and styled as desired while retaining more hair, thereby making the hair appear stronger and more vibrant. It is desirable to be able to continue these hair procedures yet reduce or stop the hair shedding that occurs during the procedure.

Hair styles that are known to result in hair loss due to pulling at the hair include hair extensions and weaves, which can be worn either to conceal hair loss, or purely for cosmetic purposes. Hair weaves create a braid around the head below the existing hairline, to which an extended-wear hairpiece, or wig, is attached. Because the hair of the braid is still growing, it requires frequent maintenance, which involves the hairpiece being removed, the natural hair braided again, and the piece snugly reattached. The tight braiding and snug hairpiece cause tension on the hair that is already at risk for falling out. Shampooing and styling is also known to result in hair loss.

One example of a disorder due to hair pulling is traction alopecia. Traction alopecia results from the chronic application of tensile force to scalp hair. The condition was described as early as 1907 in subjects from Greenland who had developed hair loss due to prolonged wearing of tight ponytails. Traditionally, the term "traction alopecia" has been related to specific hairstyles that cause increased tension on the scalp (e.g., ponytails, Afro-Caribbean hair styles with tight braiding (such as cornrows) or the tightly wound turbans of Sikh men). It has also been seen in female ballerinas. It is also seen in cultural traditions where the hair is voluntarily not cut in religious obeisance, which causes progressively increasing weight of the hair itself. Traction alopecia is mechanical in etiology, rather than androgenic. Management includes cessation of the chronic traction. However, this is unacceptable to people who favor the specific hairstyles and styling techniques that give rise to the condition.

Traction alopecia is one of the most common causes of hair loss in African American women. "Traction alopecia" includes hair loss or shedding due to increased traumatic force on hair follicles caused by hairstyle or mechanical hair procedures such as blow drying, flat ironing, hair curling and chronic brushing. Traction alopecia can also develop in patients constantly pulling their hair such as in trichotillomania. In traction alopecia, affected areas depend on the etiology of the disorder, but usually hair loss is localized on frontal and temporal scalp. According to population studies in African women, prevalence of traction alopecia varies from 17.1% in young women (6-21 years) to 31.7% in older women (18-86 years). Clinical features of traction alopecia include itching of the scalp, perifollicular erythema, scaling, folliculitis, and pustules, but it can also present as slow onset of hair loss without other symptoms. Primarily, traction alopecia is considered noncicatricial, yet excessive tension can lead to permanent alopecia, due to physical damage of hair follicles. Prolonged force on hair follicles may lead to inflammatory changes in immune cell infiltrate and fibrosis can result. Therefore, it is important to recognize the condition early, while it is still reversible.

In view of the popularity of hairstyles and hair techniques that pull at the hair and result in hair loss, there is a need for a product useful for treatment and prevention of hair loss associated with pulling on the hair.

PCT patent application WO2016/077744 entitled System and Method for Preventing Alopecia discusses treating traction alopecia by administering a composition containing an alpha-1 adrenergic receptor agonist to contract the arrector pili muscle. WO2016/077744 discusses that a suitable alpha-1 adrenergic receptor agonist is synephrine, among other compounds. p-synephrine (referred to as synephrine herein) is the primary protoalkaloid in *Citrus aurantium* (bitter orange) and in other *Citrus* species. Stohs, S. et al., Oxidative Medicine and Cellular Longevity, vol. 2011, Article ID 482973, pp. 1-9. The extract of bitter orange and synephrine have been marketed as dietary supplements purported to be a weight-loss aid and an appetite suppressant. They are also applied to the skin for pain, bruises, and bed sores. See Bitter Orange entry, National Center for Complementary and Integrative Health website, https://nccih.nih.gov/health/bitterorange (accessed Feb. 16, 2017). Bitter orange extract contains synephrine U.S. Patent App. Pub. 20080107679A1 to Dilallo et al. describes a wrinkle reduction eye serum comprising an acetyl hexapeptide and REMODULINE® cosmetic product containing bitter orange flower extract sold by Silab. REMODULINE® comprises water, propylene glycol, and bitter orange flower extract, as reported in U.S. Patent App. Pub. 20080107679A1. The eye serum comprising bitter orange extract does not include PEG-6 caprylic/capric glycerides. U.S. Patent App. Pub. 20030235595 A1 to Chen et al. discloses pharmaceutical compositions including transesterification products of oils and alcohols that include PEG-6 caprylic/capric glycerides (sold under the brand name SOFTIGEN®676 (Huels) and GLYCEROX 767 (Croda).

It is an object of the present invention to provide compositions of synephrine or bitter orange extract that when applied topically to human skin or scalp reduce hair loss due to hair pulling activities, such as shampooing, brushing, combing, styling, applying hair weaves, etc. Such compositions may require high concentrations of synephrine and/or be formulated to allow for sufficient synephrine penetration of the skin to provide effective amounts of synephrine at the hair follicle to reduce hair loss due to pulling, and to prevent or reduce damage due to traction alopecia.

SUMMARY

The present disclosure concerns compositions comprising water, synephrine, and a penetration enhancer such as caprylic/capric glycerides, preferably PEG-6 caprylic/capric glycerides. The disclosure also provides methods of reducing the shedding of hair in a person comprising applying a therapeutically effective of synephrine compositions to the scalp of the person prior to physically stressing the hair, such as prior to styling, shampooing, or brushing the hair. The disclosure also provides kits comprising a synephrine composition and a spray device, and/or a further hair care product, such as a shampoo, conditioner, oil, etc. The disclosure also provides aqueous compositions comprising at least 30% w/w synephrine and a penetration enhancer.

BRIEF DESCRIPTION OF THE DRAWINGS

FIG. 1 reports the results of a double blinded placebo controlled clinical study conducted to assess the efficacy of the composition of Example 4 (referred to as formula 01) in reducing the amount of hair on a brush during hair brushing procedures.

FIG. 2 is a graph showing synephrine delivery over time for (1) a synephrine composition containing PEG-6 caprylic/capric glycerides and (2) a synephrine composition containing di(ethylene glycol) ethyl ether.

FIG. 3 shows an experimental set up for testing stability of a synephrine composition.

FIG. 4 shows stability test results for the synephrine composition of FIG. 3.

DETAILED DESCRIPTION

The inventions herein relate to (1) compositions of synephrine including without limitation of bitter orange extract (extract of *Citrus Aurantium* L.), (2) methods of preparing the compositions, (3) methods of administering the compositions, (4) methods of treatment or prevention of alopecia and other hair loss disorders, such as traction alopecia, by applying or administering therapeutically effective amounts of the compositions, (5) methods of reducing hair loss resulting from procedures that pull the hair away from the follicle, such as washing, combing, brushing, styling, pressing, etc. and (6) kits comprising the inventive compositions and at least one additional hair care product or container for administering the inventive composition.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

As used herein, the term "traction alopecia" means a form of alopecia (hair loss or hair shedding) associated with mechanical forces that pull the hair such as hair brushing hair combing, flat ironing, wearing of extensions, hair braiding, and ponytail style hair. Under this definition, although chronic traction on the hair can lead to traction alopecia, the mechanical forces that pull the hair do not necessarily need to be chronic to lead to hair loss or excessive shedding.

As used herein, the terms "prevent" or "prevention" and other derivatives of the words, when used in reference to alopecia, e.g., traction alopecia, refer to a reduced likelihood of alopecia in an individual receiving a given treatment relative to that of a similar individual at risk for alopecia but not receiving that treatment. As such, the terms "prevent" and "prevention" encompass a treatment that results in a lesser degree of alopecia, e.g., traction alopecia, than would be otherwise expected for a given individual.

Efficacy for reducing hair loss, mitigating hair loss, and prevention of traction alopecia can be established through controlled studies in which a subject is administered a treatment (e.g., a topical treatment) at one site likely to experience or exhibit hair loss or hair shedding (e.g., for traction alopecia, a site at which hair is pulled for an extended period of time) but not at another site subjected to the same conditions. Under these circumstances, if the site receiving the topical treatment undergoes less hair loss over time relative to the untreated site, e.g., at least 5% less, at least 10% less, at least 15% less, at least 20% less, at least 25% less, at least 30% less, at least 35% less, at least 40% less, at least 45% less, at least 50% less or beyond, the treatment is effective for reducing hair loss. Determination of efficacy also may involve the measurement or detection of pilomotor stimulation, which can be performed, at its simplest, by observation of the area at the base of the hair shaft to determine whether the arrector pili ("AP") muscle has contracted. A composition that induces arrector pili contraction causes the hair follicle to "stand up" and causes puckering of the skin around the hair shaft commonly referred to as "goose bumps." Thus, if a composition is applied and the hair stands up, goose bumps form, or both, the composition has stimulated the arrector pili. Measurement of the strength of arrector pili muscle contraction can be performed via myograph adapted for that purpose. Examples are described in, e.g., Zeveke & Gladysheva, Bull. Exp. Biol. Med. 71: 102-105 (1971); Hellmann, J. Physiol. 169: 603-620 (1963); Wyness L A, McNeill G, Prescott G L. Trichotillometry: the reliability and practicality of hair pluckability as a method of nutritional assessment. Nutr J 2007: 6: 9; and Chase E S, Weinsier R L, Laven G T, Krumdieck C L. Trichotillometry: the quantitation of hair pluckability as a method of nutritional assessment. Am J Clin Nutr 1981: 34(10): 2280-2286. Other systems to measure the strength of the arrector pili muscle can use a trichotillometer or a device used to measure tensile forces.

As used herein, the terms "treat," "treatment," or "treating" refers to reversing, inhibiting, slowing down or stopping the progression or severity of a disease or condition, e.g., traction alopecia or other form of alopecia. Treatment of alopecia, and particularly traction alopecia, is generally "effective" if hair loss or hair shedding is slowed or stopped, or hair regrows at a faster rate than hair is lost. The methods of showing efficacy for prevention of alopecia discussed above are also applicable for showing efficacy of treatment of alopecia.

As used herein, the term "mitigate" or "mitigating" in the context of hair loss or hair shedding means to reduce the amount of hair removed or hair that falls out, such as reducing the amount of hair shedding when a cosmetic procedure is applied to the hair.

As used herein, the term "epilatory" relates to the removal of hair. As used herein, the term "increasing epilatory force" refers to any treatment that increases the physical force required to remove a hair. The increase in force can be viewed as at least a partial balancing of a traction force by the force exerted by the arrector pili muscle the vector direction of the arrector pili muscle's force of contraction need not necessarily be directly opposed to a traction force on the hair shaft to increase the epilatory force required to remove the hair, but the net effect is that the muscle provides at least a partial counter-acting force to the traction force, whether it directly pulls back on the hair or simply holds the hair or hair follicle more tightly in place. An increase in epilatory force can be measured in several ways, including empirically, through a reduction in traction alopecia (e.g., 10% or less reduction in hair loss) despite continued or ongoing traction, or through measurement of actual force exerted on the hair follicle, e.g., with a myograph, trichotilometer, or a device used to measure tensile forces.

As used herein the term "comprising" or "comprises" is used in reference to compositions, methods, etc. refers to component(s) or method steps that are present in the method or composition, yet allows for the composition, method, etc. to also include unspecified elements.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Compositions of Synephrine

The compositions of the present disclosure contain synephrine. A source of synephrine that may be used in the compositions of the technology described herein is *Citrus Aurantium*, conventionally known as bitter orange, seville orange, sour orange, bigarade orange, or marmalade orange. Substantially all of the synephrine in bitter orange extract is in the R(−) enantiomeric form. The present disclosure encompasses formulations of synephrine in which the synephrine is present in the R(−) enantiomer, in the S (+) enantiomer, in mixtures of both R and S enantiomers, and as a racemic mixture of R and S enantiomers.

"Bitter Orange Extract" as used herein is a product derived from *Citrus Aurantium Amara* (bitter orange) that contains about 6-99% by weight of R (−) synephrine. The extract may be of the peel powder.

Without limiting the invention in any way, Applicants believe that synephrine acts to prevent or treat hair loss from hair pulling and disorders characterized by mechanical pulling on the hair such as traction alopecia by increasing the opposing force exerted on the hair follicle by inducing contraction of the arrector pili (AP) muscle. Each follicular unit contains an AP smooth muscle unit anchoring the hair to the epidermis. The contraction of the AP muscle erects the hair and contracts the smooth muscle surrounding the root and thus reduces the force on the root as well as increases the eplilation force required to remove the hair. When the smooth muscle is relaxed, the muscle does not supply much restraining force and the follicle can be removed easily. When the smooth muscle or arrector pili (AP) contracts, the follicle stands up and is restrained by additional force from the smooth muscle rather than just primarily the surrounding connective tissue of the dermis. Accordingly, the smooth muscle can provide more retention force in opposition to a force that would pull on the hair to dislodge the follicle if it is contracted. Thus, by contracting the arrector pili (AP) muscle, it is believed that the root can be more firmly grounded into the dermis of the skin preventing the mechanical strain from damaging the root and dermis, i.e. requiring a larger epilation force for removal of the hair follicle. Thus, compounds or agents that stimulate contraction of the AP muscle can reduce hair loss by increasing the force required to remove the hair. By increasing the opposing force exerted on the hair follicle during activities that pull at the hair, the present compositions improve the sturdiness or stiffness of individual strands of hair. The overall effect is to provide stronger, thicker-looking hair than if the procedures had been applied without the compositions of the present disclosure.

In some aspects, then, the technology described herein relates to the reduction of the force exerted on the root of a hair. In practice, this "reduction" in force is more akin to providing a better balancing force against a traction on the hair itself—that is, the treatments described herein will not necessarily reduce the amount of traction on the hair, but by stimulating the contraction of the arrector pili muscles, the treatments provide a force that at least partially counters the effect of the traction or pulling force, thereby protecting the root against the epilatory effect of the traction.

Accordingly, disclosed herein are methods for contracting the smooth muscle cells or arrector pili while a patient is wearing a hair extension, wig, a tightly woven or pulling hairstyle, combing their hair, or engaging in other behavior that pulls back on the follicles of the hair. The AP muscle may be contracted by applying the compositions described herein. The compositions according to the present disclosure comprise synephrine and water. In one embodiment, the compositions further comprise a penetration enhancer, such as caprylic/capric glyceride, preferably PEG-6 caprylic/capric glyceride. Applicants have discovered that high concentrations of synephrine, such as without limitation of bitter orange extract, are difficult to formulate into stable compositions with water. Surprisingly, Applicants have found that formulations of synthetically prepared synephrine (synephrine HCl) can be produced with higher synephrine concentrations than compositions of synephrine that is obtained from bitter orange extract. Furthermore, the hair loss and hair shedding described have been found by Applicants to be best addressed and mitigated by applying compositions in which a relatively high amount of synephrine is delivered through the dermis at the follicle to the base of the hair follicle. Compositions have been discovered that provide for high levels of synephrine to penetrate the dermis and reach the base of the hair follicle. In particular, the inventive compositions contain or comprise penetration enhancers, preferably caprylic/capric glyceride and derivatives thereof.

In one embodiment, the composition comprises between about 10% to about 60% by weight of synephrine and between about 10% and about 60% water by weight. In other embodiments, synephrine is present at about 10% to 20%, and water is present at about 10% to 20%. In other embodiments, synephrine is present at about 10% to 20% and water at about 10% to 30%; synephrine is present at about 20% to 30%, and water is present at about 10% to about 40%; synephrine is present at about 30% to 40%, and water is present at about 10% to about 50%; synephrine is present at about 40% to 50%, and water is present at about 20% to about 40%; and synephrine is present at about 30% to 50%, and water is present at about 10% to about 40%. For purposes of these weight ranges, the weight of synephrine is based on the weight of synephrine in free base form. Other forms, such as salt forms, of synephrine may be used, in which cases the weight percentage above reflects the equivalent weight of synephrine free base. Naturally sourced synephrine, such as that obtained from bitter orange extract, has a lower molecular weight (167.2) than a salt form of synephrine that is produced synthetically, synephrine HCl (203.7). As such, more of the salt form is needed than the freebase form to have the same concentration of the synephrine molecule in solution. For example, a 37% w/w synephrine HCl composition contains the equivalent synephrine content as a 32% w/w synephrine free base composition. As used herein, a 25-35% w/w synephrine composition encompasses a composition containing 37% synephrine HCl because its equivalent synephrine weight percentage is 30% w/w, which is within the range of 25-35%.

In a further embodiment, the composition further comprises caprylic/capric glyceride, such as PEGylated caprylic/capric glycerides, including without limitation PEG-6 caprylic/capric glyceride such as Acconon® CC-6 PEG-6 caprylic/capric glycerides (supplied by Abitec Corporation) and Tegosoft® GMC 6 PEG-6 caprylic/capric glycerides (supplied by Evonik Industries AG). In some embodiments, the composition comprises about 20% to about 40% by weight of water, about 25% to about 35% by weight of synephrine, and about 5% to about 40% by weight of PEGylated caprylic/capric glyceride. The composition may comprise at least one additional additive.

In one embodiment, the composition comprises between about 10% to about 60% by weight of synephrine, between about 10% and about 60% by weight water, and between about 5% and about 30% by weight PEGylated caprylic/capric glyceride. In other embodiments, synephrine is present at about 10% to 20%, water is present at about 10% to 20%, and PEGylated caprylic/capric glyceride is present at about 5% to 20%. In other embodiments, synephrine is present at about 10% to 20%, water at about 10% to 30%, and PEGylated caprylic/capric glyceride at about 5% to 20%. In a further embodiment, synephrine is present at about 20% to 30%, water is present at about 10% to about 40% and PEGylated caprylic/capric glyceride is present at about 5% to 20%. In a further embodiment, synephrine is present at about 30% to 40%, water is present at about 10% to about 50%, and PEGylated caprylic/capric glyceride is present at about 5% to about 20%. In yet a further embodiment, synephrine is present at about 40% to 50%, water is present at about 20% to about 40%, and PEGylated caprylic/capric glyceride is present at about 5% to about 20%. In yet a further embodiment, synephrine is present at about 30% to 50%, water is present at about 10% to about 40%, and PEGylated caprylic/capric glyceride is present at about 5% to about 15%. For purposes of these weight ranges, if a product other than synephrine free base is used, the weight percentage corresponds to the equivalent weight percentage of synephrine in free base form.

Typically, synthetically produced synephrine comprises S-(+)-synephrine and R-(−)-synephrine. Brown, C. M. et al., "Activities of octopamine and synephrine stereoisomers on alpha-adrenoceptors," Br. J. Pharmacol. (1988), 93, 417-429 describes the activities of the stereoisomers of p-synephrine (referred to as synephrine herein) on postjunctional alpha1 alpha2-adrenoceptors. The potency of the (+) form was one to two orders of magnitude less than the (−) form on these two adrenoceptors. Accordingly, Applicants believe that R-(−)-synephrine has greater activity for the treatment and conditions disclosed herein than S-(+)-synephrine. However, using the commercial synephrine sources and the experiments described herein, an efficacy difference has not been noted experimentally.

The synephrine used in the inventions disclosed herein is p-synephrine, and may be obtained from natural sources or synthetically produced, and may be a salt, solvate or hydrate of p-synephrine. The synephrine that may be used in the inventive compositions and methods herein includes without limitation bitter orange extract; a racemic mixture of R-(−)-synephrine and S-(+)-synephrine; synephrine that is greater than 40% R-(−)-synephrine and 60% or less by weight S-(+)-synephrine; synephrine that is greater than 50% R-(−)-synephrine and 50% or less by weight S-(+)-synephrine; synephrine that is greater than 60% R-(−)-synephrine and 40% or less by weight S-(+)-synephrine; synephrine that is greater than 70% R-(−)-synephrine and 30% or less by weight S-(+)-synephrine; synephrine that is greater than 90% R-(−)-synephrine and 10% or less by weight S-(+)-synephrine; synephrine that is greater than 95% R-(−)-synephrine; synephrine that is greater than 98% R-(−)-synephrine; synephrine that is substantially all R-(−)-synephrine; or any mixture of R-(−)-synephrine and S-(+)-synephrine.

In some embodiments of the present disclosure, the composition contains synephrine or synephrine HCl, each in any enantiomeric form or mixtures thereof, as a weight percentage based on the total weight of the composition of about 10% to about 60%, about 15% to about 60%, about 20% to about 60%, about 25% to about 60%, 30% to about 60%, about 10% to about 55%, about 10% to about 50%, about 15% to about 50%, about 20% to about 50%, about 25% to about 50%, about 30% to about 50%, about 35% to about 50%, about 40% to about 50%, about 45% to about 50%, about 10% to about 40%, about 15% to about 40%, about 20% to about 40%, about 25% to about 40%, about 15% to about 35%, about 20% to about 35%, about 25% to about 35%, about 20% to about 30%, about 30% to about 35%, about 20% to about 70%, about 25% to about 70%, about 30% to about 70%, about 35% to about 70%, about 40% to about 70%, about 45% to about 70%, about 50% to about 70%, about 55% to about 70%, about 20% to about 65%, about 25% to about 65%, about 30% to about 65%, about 35% to about 65%, about 40% to about 65%, about 45% to about 65%, about 50% to about 65%, or about 55% to about 65%. Other forms of synephrine, such as other salt forms than HCl, may be used. The appropriate weight ranges for other forms of synephrine should be determined based on the guidance above of weight ranges for synephrine and synephrine HCl.

The compositions of the present disclosure contain water, as a weight percentage based on the total weight of the composition, of about 60%, about 15% to about 60%, about 20% to about 60%, about 25% to about 60%, 30% to about 60%, about 10% to about 55%, about 10% to about 50%, about 15% to about 50%, about 20% to about 50%, about 25% to about 50%, about 30% to about 50%, about 35% to about 50%, about 40% to about 50%, about 45% to about 50%, about 10% to about 40%, about 15% to about 40%, about 20% to about 40%, about 25% to about 40%, about 15% to about 35%, about 20% to about 35%, about 25% to about 35%, about 20% to about 30%, about 30% to about 35%, about 20% to about 70%, about 25% to about 70%, about 30% to about 70%, about 35% to about 70%, about 40% to about 70%, about 45% to about 70%, about 50% to about 70%, about 55% to about 70%, about 20% to about 65%, about 25% to about 65%, about 30% to about 65%, about 35% to about 65%, about 40% to about 65%, about 45% to about 65%, about 50% to about 65%, or about 55% to about 65%. The composition may comprise about 10% to about 60%, about 15% to about 60%, about 20% to about 60%, about 25% to about 60%, 30% to about 60%, about 10% to about 55%, about 10% to about 50%, about 15% to about 50%, about 20% to about 50%, about 25% to about 50%, about 30% to about 50%, about 35% to about 50%, about 40% to about 50%, about 45% to about 50%, about 10% to about 40%, about 15% to about 40%, about 20% to about 40%, about 25% to about 40%, about 15% to about 35%, about 20% to about 35%, about 25% to about 35%, about 20% to about 30%, about 30% to about 35%, about 20% to about 70%, about 25% to about 70%, about 30% to about 70%, about 35% to about 70%, about 40% to about 70%, about 45% to about 70%, about 50% to about 70%, about 55% to about 70%, about 20% to about 65%, about 25% to about 65%, about 30% to about 65%, about 35% to about 65%, about 40% to about 65%, about 45% to about 65%, about 50% to about 65%, about 55% to about 65%, by weight of water.

Embodiments of the present disclosure include compositions comprising water, synephrine, and a penetration enhancer. In some embodiments, the composition further comprises additives, such as components to improve the miscibility of the composition. In some embodiments, the composition further comprises at least one preservative.

A penetration enhancer or permeation enhancer is an agent used to increase the permeability of the stratum corneum ("SC"). The SC is the outer most layer of skin. Cornification of the SC makes it a good barrier to most water soluble molecules. Penetration enhancers typically disrupt the barrier function of the SC. After passage through the SC, molecules are free to diffuse into deeper tissues. A chemical penetration enhancer increases skin permeability by reversibly altering the physiochemical nature of the tissue to reduce its diffusional resistance. According to one or more embodiments of the present invention a penetration enhancer is incorporated into the composition. It is to be understood that components identified herein as penetration enhancers may have other roles in the formulation also, such as act as an emulsifying agent, secondary surfactant, or emollient.

Examples of penetration enhancers according to the present invention include: polyols, such as propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, and glycerol; sulfoxides, such as dimethylsulfoxide (DMSO), dimethylformanide, methyl dodecyl sulfoxide, dimethylacetamide; monooleate of ethoxylated glycerides (with 8 to 10 ethylene oxide units); azone (1-dodecylazacycloheptan-2-one), 2-(n-nonyl)-1,3-dioxolane; esters, such as isopropyl myristate/palmitate, ethyl acetate, butyl acetate, methyl proprionate, capric/caprylic triglycerides, PEG-6 capylic/capric glycerides, PEG-7 caprylic/capric glycerides, mixed decanoyl and octanoyl glycerides, octylmyristate, dodecyR-(−)-myristate; myristyl alcohol, lauryl alcohol, lauric acid, lauryl lactate ketones; amides, such as acetamide oleates such as triolein; various surfactants, such as sodium lauryl sulfate; various alkanoic acids such as caprylic acid; lactam compounds, such as azone; alkanols, such as oleyl alcohol; dialkylamino acetates, and mixtures thereof. Other penetration enhancers that may be used are cyclodextrins and related compounds. Cyclodextrins are structurally related cyclic oligomaltoses.

In the preferred embodiments, the penetration enhancer is PEG-6 capylic/capric glycerides, such as the products sold under the trade names ACCONON® CC-6 and Tegosoft® GMC 6. The composition may comprise about 4% to about 20%, about 5% to about 20%, about 5% to about 15%, about 6% to about 15%, about 7% to about 15%, about 8% to about 15%, about 9% to about 15%, about 10% to about 15%, about 11% to about 15%, about 12% to about 15%, about 5% to about 14%, about 6% to about 14%, about 7% to about 14%, about 8% to about 14%, about 9% to about 14%, about 5% to about 13%, about 6% to about 13%, about 7% to about 13%, about 8% to about 13%, about 9% to about 13%, about 5% to about 12%, about 6% to about 12%, about 7% to about 12%, about 8% to about 12%, about 9% to about 12%, about 10% to about 12%, about 5% to about 11%, about 6% to about 11%, about 7% to about 11%, about 8% to about 11%, about 9% to about 11%, about 10% to about 11%, about 5% to about 10%, about 6% to about 10%, about 7% to about 10%, about 8% to about 10%, about 9% to about 10%, or about 30% to about 35% by weight of a penetration enhancer such as caprylic/capric glycerides or PEGylated caprylic/capric glycerides, preferably PEG-6 caprylic/capric glycerides, based on the total weight of the composition.

Compositions comprising about 10% to about 20% by weight of synephrine and about 35% to about 60% by weight of water may comprise about 20% to about 40%, about 25% to about 40%, about 30% to about 40%, about 35% to about 40%, about 20% to about 35%, about 25% to about 35%, about 30% to about 35%, about 20% to about 30%, about 25% to about 30%, or about 20% to about 25% by weight of penetration enhancer such as caprylic/capric glycerides or PEGylated caprylic/capric glycerides, preferably PEG-6 caprylic/capric glycerides.

Compositions comprising about 15% to about 25% by weight of synephrine and about 30% to about 55% by weight of water may comprise about 15% to about 40%, about 20% to about 40%, about 25% to about 40%, about 30% to about 40%, about 35% to about 40%, about 15% to about 35%, 20% to about 35%, about 25% to about 35%, about 30% to about 35%, about 15% to about 30%, about 20% to about 30%, about 25% to about 30%, about 15% to about 25%, about 20% to about 25%, or about 15% to about 20% by weight of penetration enhancer such as caprylic/capric glycerides or PEGylated caprylic/capric glycerides, preferably PEG-6 caprylic/capric glycerides.

Compositions comprising about 20% to about 30% by weight of synephrine and about 25% to about 50% by weight of water may comprise about 10% to about 40%, 15% to about 40%, about 20% to about 40%, about 25% to about 40%, about 30% to about 40%, about 35% to about 40%, about 10% to about 35%, about 15% to about 35%, 20% to about 35%, about 25% to about 35%, about 30% to about 35%, about 10% to about 30%, about 15% to about 30%, about 20% to about 30%, about 25% to about 30%, about 10% to about 25%, about 15% to about 25%, about 20% to about 25%, about 10% to about 20%, about 15% to about 20%, or about 10% to about 15% by weight of penetration enhancer such as caprylic/capric glycerides or PEGylated caprylic/capric glycerides, preferably PEG-6 caprylic/capric glycerides.

Compositions comprising about 30% to about 40% by weight of synephrine and about 40% to about 55% by weight of water may comprise about 5% to about 35%, about 10% to about 35%, about 15% to about 35%, 20% to about 35%, about 25% to about 35%, about 30% to about 35%, about 5% to about 30%, about 10% to about 30%, about 15% to about 30%, about 20% to about 30%, about 25% to about 30%, about 5% to about 25%, about 10% to about 25%, about 15% to about 25%, about 20% to about 25%, about 5% to about 20%, about 10% to about 20%, about 15% to about 20%, about 3% to about 15%, about 4% to about 15%, about 5% to about 15%, about 6% to about 15%, 7% to about 15%, about 8% to about 15%, about 9% to about 15%, about 10% to about 15%, about 11% to about 15%, about 12% to about 15%, about 13% to about 15%, about 14% to about 15%, about 3% to about 14%, about 4% to about 14%, about 5% to about 14%, about 6% to about 14%, about 7% to about 14%, about 8% to about 14%, about 9% to about 14%, about 10% to about 14%, about 11% to about 14%, about 12% to about 14%, about 13% to about 14%, about 3% to about 13%, about 4% to about 13%, about 5% to about 13%, about 6% to about 13%, about 7% to about 13%, about 8% to about 13%, about 9% to about 13%, about 3% to about 12%, about 4% to about 12%, about 5% to about 12%, about 6% to about 12%, about 7% to about 12%, about 8% to about 12%, about 9% to about 12%, about 10% to about 12%, about 11% to about 12%, about 3% to about 11%, about 4% to about 11%, about 5% to about 11%, about 6% to about 11%, about 7% to about 11%, about 8% to about 11%, about 9% to about 11%, about 10% to about 11%, about 3% to about 10%, about 4% to about 10%, about 5% to about 10%, about 6% to about 10%, about 7% to about 10%, about 8% to about 10%, about 9% to about 10%, about 3% to about 9%, about 4% to about 9%, about 5% to about 9%, about 6% to about 9%, about 7% to about 9%, about 8% to about 9%, about 3% to about 8%, about 4% to about 8%, about 5% to about 8%, about 6% to about 8%, about 7% to about 8%, about 3% to about 7%, about 4% to about 7%, about 5% to about 7%, about 6% to about 7%, about 3% to about 6%, about 4% to about 6%, about 5% to about 6%, about 3% to about 5%, about 4% to about 5%, or about 3% to about 4% by weight of penetration enhancer such as caprylic/capric glycerides or PEGylated caprylic/capric glycerides, preferably PEG-6 caprylic/capric glycerides.

Compositions comprising about 30% to about 40% by weight of synephrine and about 25% to about 50% by weight of water may comprise about 5% to about 30%, about 10% to about 30%, about 15% to about 30%, about 20% to about 30%, about 25% to about 30%, about 5% to about 25%, about 10% to about 25%, about 15% to about 25%, about 20% to about 25%, about 5% to about 20%, about 10% to about 20%, about 15% to about 20%, about 3% to about 15%, about 4% to about 15%, about 5% to about 15%, about 6% to about 15%, 7% to about 15%, about 8% to about 15%, about 9% to about 15%, about 10% to about 15%, about 11% to about 15%, about 12% to about 15%, about 13% to about 15%, about 14% to about 15%, about 3% to about 14%, about 4% to about 14%, about 5% to about 14%, about 6% to about 14%, about 7% to about 14%, about 8% to about 14%, about 9% to about 14%, about 10% to about 14%, about 11% to about 14%, about 12% to about 14%, about 13% to about 14%, about 3% to about 13%, about 4% to about 13%, about 5% to about 13%, about 6% to about 13%, about 7% to about 13%, about 8% to about 13%, about 9% to about 13%, about 3% to about 12%, about 4% to about 12%, about 5% to about 12%, about 6% to about 12%, about 7% to about 12%, about 8% to about 12%, about 9% to about 12%, about 10% to about 12%, about 11% to about 12%, about 3% to about 11%, about 4% to about 11%, about 5% to about 11%, about 6% to about 11%, about 7% to about 11%, about 8% to about 11%, about 9% to about 11%, about 10% to about 11%, about 3% to about 10%, about 4% to about 10%, about 5% to about 10%, about 6% to about 10%, about 7% to about 10%, about 8% to about 10%, about 9% to about 10%, about 3% to about 9%, about 4% to about 9%, about 5% to about 9%, about 6% to about 9%, about 7% to about 9%, about 8% to about 9%, about 3% to about 8%, about 4% to about 8%, about 5% to about 8%, about 6% to about 8%, about 7% to about 8%, about 3% to about 7%, about 4% to about 7%, about 5% to about 7%, about 6% to about 7%, about 3% to about 6%, about 4% to about 6%, about 5% to about 6%, about 3% to about 5%, about 4% to about 5%, or about 3% to about 4% by weight of penetration enhancer such as caprylic/capric glycerides or PEGylated caprylic/capric glycerides, preferably PEG-6 caprylic/capric glycerides.

Compositions comprising more than about 40% by weight of synephrine may comprise no penetration enhancer. Preferably, such formulations with no penetration enhancer comprise at least 40%, 45%, 50%, 55%, 60%, 65% or 70% w/w synephrine.

Additives

The synephrine compositions of the present disclosure also may include additives. One additive that is present in some embodiments is glycolic acid, which is available as an aqueous solution, such as 70% glycolic acid by weight in aqueous solution. The following compositions comprise glycolic acid in which the weight percentages given are the weight percentage of 70% glycolic acid in aqueous solution based on the weight of the total composition. Other concentrations of glycolic acid solutions may be used within the scope of the invention. One composition of the present disclosure comprises between about 10% to about 60% by weight of synephrine, between about 10% and about 60% by weight water, between about 5% and about 30% by weight PEGylated or nonPEGylated caprylic/capric glyceride, and between about 5% to about 25% glycolic acid solution. In other embodiments, synephrine is present at about 40% to 50%, water is present at about 30% to 50%, PEGylated caprylic/capric glyceride is present at about 5% to 20%, and glycolic acid solution is present at between about 5% to about 10%. In other embodiments, synephrine is present at about 30% to 50%, water at about 20% to 40%, PEGylated caprylic/capric glyceride at about 5% to 20%, and glycolic acid solution is present at between about 5% to about 25%. In a further embodiment, synephrine is present at about 20% to 30%, water is present at about 10% to about 40%, PEGylated caprylic/capric glyceride is present at about 5% to 20%, and glycolic acid solution is present at about 5% to about 20%.

The composition may comprise as a further additive a diol, such as a $C_3$ to $C_8$ alkyl diol, including without limitation propanediol, such as 1,3 propanediol or 1,2-propanediol, which diol preferably functions as a preservative. The diol, preferably propanediol, is present in the composition at about 0.05% to about 10%, about 0.05% to about 9%, about 0.05% to about 8%, about 0.05% to about 7%, about 0.05% to about 6%, about 0.05% to about 5%, about 0.05% to about 4%, about 0.05% to about 3.5%, about 0.05% to about 3%, about 0.05% to about 2.5%, about 0.05% to about 2%, about 0.05% to about 1%, about 0.8% to about 10%, about 0.8% to about 9%, about 0.8% to about 8%, about 0.8% to about 7%, about 0.8% to about 6%, about 0.8% to about 5%, about 0.8% to about 4%, about 0.8% to about 3.5%, about 0.8% to about 3%, about 0.8% to about 2.5%, about 0.8% to about 2%, about 0.8% to about 1%, about 1% to about 10%, about 1% to about 9%, about 1% to about 8%, about 1% to about 7%, about 1% to about 6%, about 1% to about 5%, about 1% to about 4%, about 1% to about 3.5%, about 1% to about 3%, about 1% to about 2.5%, about 1% to about 2%, about 1.2% to about 10%, about 1.2% to about 9%, about 1.2% to about 8%, about 1.2% to about 7%, about 1.2% to about 6%, about 1.2% to about 5%, about 1.2% to about 4%, about 1.2% to about 3.5%, about 1.2% to about 3%, about 1.2% to about 2.5%, about 1.2% to about 2%, about 1.5% to about 10%, about 1.5% to about 9%, about 1.5% to about 8%, about 1.5% to about 7%, about 1.5% to about 6%, about 1.5% to about 5%, about 1.5% to about 4%, about 1.5% to about 3.5%, about 1.5% to about 3%, about 1.5% to about 2.5%, about 1.5% to about 2%, about 1.7% to about 10%, about 1.7% to about 9%, about 1.7% to about 8%, about 1.7% to about 7%, about 1.7% to about 6%, about 1.7% to about 5%, about 1.7% to about 4%, about 1.7% to about 3.5%, about 1.7% to about 3%, about 1.7% to about 2.5%, about 1.7% to about 2%, about 1.8% to about 10%, about 1.8% to about 9%, about 1.8% to about 8%, about 1.8% to about 7%, about 1.8% to about 6%, about 1.8% to about 5%, about 1.8% to about 4%, about 1.8% to about 3.5%, about 1.8% to about 3%, about 1.8% to about 2.5%, about 1.8% to about 2%, about 2% to about 10%, about 2% to about 9%, about 2% to about 8%, about 2% to about 7%, about 2% to about 6%, about 2% to about 5%, about 2% to about 4%, about 2% to about 3.5%, about 2% to about 3%, about 2% to about 2.5%, about 2% to about 2%, about 2% to about 1%, about 2.1% to about 10%, about 2.1% to about 9%, about 2.1% to about 8%, about 2.1% to about 7%, about 2.1% to about 6%, about 2.1% to about 5%, about 2.1% to about 4%, about 2.1% to about 3.5%, about 2.1% to about 3%, about 2.1% to about 2.5%, about 2.2% to about 10%, about 2.2% to about 9%, about 2.2% to about 8%, about 2.2% to about 7%, about 2.2% to about 6%, about 2.2% to about 5%, about 2.2% to about 4%, about 2.2% to about 3.5%, about 2.2% to about 3%, about 2.2% to about 2.5%, about 2.3% to about 10%, about 2.3% to about 9%, about 2.3% to about 8%, about 2.3% to about 7%, about 2.3% to about 6%, about 2.3% to about 5%, about 2.3% to about 4%, about 2.3% to about 3.5%, about 2.3% to about 3%, about 2.3% to about 2.5%, about 2.4% to about 10%, about 2.4% to about 9%, about 2.4% to about 8%, about 2.4% to about 7%, about 2.4% to about 6%, about 2.4% to about 5%, about 2.4% to about 4%, about 2.4% to about 3.5%, about 2.4% to about 3%, about 2.4% to about 2.5%, about 2.5% to about 10%, about 2.5% to about 9%, about 2.5% to about 8%, about 2.5% to about 7%, about 2.5% to about 6%, about 2.5% to about 5%, about 2.5% to about 4%, about 2.5% to about 3.5%, about 2.5% to about 3%, about 2.6% to about 10%, about 2.6% to about 9%, about 2.6% to about 8%, about 2.6% to about 7%, about 2.6% to about 6%, about 2.6% to about 5%, about 2.6% to about 4%, about 2.6% to about 3.5%, about 2.6% to about 3%, about 2.7% to about 10%, about 2.7% to about 9%, about 2.7% to about 8%, about 2.7% to about 7%, about 2.7% to about 6%, about 2.7% to about 5%, about 2.7% to about 4%, about 2.7% to about 3.5%, about 2.7% to about 3%, about 2.8% to about 10%, about 2.8% to about 9%, about 2.8% to about 8%, about 2.8% to about 7%, about 2.8% to about 6%, about 2.8% to about 5%, about 2.8% to about 4%, about 2.8% to about 3.5%, about 2.8% to about 3%, about 2.9% to about 10%, about 2.9% to about 9%, about 2.9% to about 8%, about 2.9% to about 7%, about 2.9% to about 6%, about 2.9% to about 5%, about 2.9% to about 4%, about 2.9% to about 3.5%, about 2.9% to about 3%, about 3% to about 10%, about 3% to about 9%, about 3% to about 8%, about 3% to about 7%, about 3% to about 6%, about 3% to about 5%, about 3% to about 4%, about 3% to about 3.5%, about 3% to about 3%, about 3% to about 2.5%, about 3% to about 2%, about 3% to about 1%, about 3.1% to about 10%, about 3.1% to about 9%, about 3.1% to about 8%, about 3.1% to about 7%, about 3.1% to about 6%, about 3.1% to about 5%, about 3.1% to about 4%, about 3.1% to about 3.5%, about 3.2% to about 10%, about 3.2% to about 9%, about 3.2% to about 8%, about 3.2% to about 7%, about 3.2% to about 6%, about 3.2% to about 5%, about 3.2% to about 4%, about 3.2% to about 3.5%, about 3.3% to about 10%, about 3.3% to about 9%, about 3.3% to about 8%, about 3.3% to about 7%, about 3.3% to about 6%, about 3.3% to about 5%, about 3.3% to about 4%, about 3.3% to about 3.5%, about 3.4% to about 10%, about 3.4% to about 9%, about 3.4% to about 8%, about 3.4% to about 7%, about 3.4% to about 6%, about 3.4% to about 5%, about 3.4% to about 4%, about 3.4% to about 3.5%, about 3.5% to about 10%, about 3.5% to about 9%, about 3.5% to about 8%, about 3.5% to about 7%, about 3.5% to about 6%, about 3.5% to about 5%, about 3.5% to about 4%, about 3.5% to about 3.9%, about 3.5% to about 3.8%, about 3.5% to about 3.7%, about 3.5% to about 3.6%, about 3.6% to about 10%, about 3.6% to about 9%, about 3.6% to about 8%, about 3.6% to about 7%, about 3.6% to about 6%, about 3.6% to about 5%, about 3.6% to about 4%, about 3.6% to about 3.9%, about 3.6% to about 3.8%, about 3.6% to about 3.7%, about 3.7% to about 10%, about 3.7% to about 9%, about 3.7% to about 8%, about 3.7% to about 7%, about 3.7% to about 6%, about 3.7% to about 5%, about 3.7% to about 4%, about 3.7% to about 3.9%, about 3.7% to about 3.8%, about 3.8% to about 10%, about 3.8% to about 9%, about 3.8% to about 8%, about 3.8% to about 7%, about 3.8% to about 6%, about 3.8% to about 5%, about 3.8% to about 4%, about 3.8% to about 3.9%, about 3.9% to about 10%, about 3.9% to about 9%, about 3.9% to about 8%, about 3.9% to about 7%, about 3.9% to about 6%, about 3.9% to about 5%, about 3.9% to about 4% about 4% to about 10%, about 4% to about 9%, about 4% to about 8%, about 4% to about 7%, about 4% to about 6%, about 4% to about 5%, about 4% to about 4.5%, about 4.5% to about 10%, about 4.5% to about 9%, about 4.5% to about 8%, about 4.5% to about 7%, about 4.5% to about 6%, about 4.5% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% by weight of the total composition.

The composition may also comprise phenoxyethanol ethylhexylglycerin, (such as the product EUXYL PE 9010 sold by Schuelke Inc.), which acts as a preservative, in a weight percent as percentage of the total weight of the aqueous composition of about 0.05% to about 5%, about 0.05% to about 4%, about 0.05% to about 3%, about 0.05% to about 2%, about 0.05% to about 1.9%, about 0.05% to about 1.8%, about 0.05% to about 1.7%, about 0.05% to about 1.6%, about 0.05% to about 1.5%, about 0.05% to about 1.4%, about 0.05% to about 1.3%, about 0.05% to about 1.2%, about 0.05% to about 1.1%, about 0.05% to about 1%, about 0.05% to about 0.9%, about 0.05% to about 0.8%, about 0.05% to about 0.7%, about 0.05% to about 0.6%, about 0.05% to about 0.5%, about 0.1% to about 5%, about 0.1% to about 4%, about 0.1% to about 3%, about 0.1% to about 2%, about 0.1% to about 1.9%, about 0.1% to about 1.8%, about 0.1% to about 1.7%, about 0.1% to about 1.6%, about 0.1% to about 1.5%, about 0.1% to about 1.4%, about 0.1% to about 1.3%, about 0.1% to about 1.2%, about 0.1% to about 1.1%, about 0.1% to about 1%, about 0.1% to about 0.9%, about 0.1% to about 0.8%, about 0.1% to about 0.7%, about 0.1% to about 0.6%, about 0.1% to about 0.5%, about 0.2% to about 5%, about 0.2% to about 4%, about 0.2% to about 3%, about 0.2% to about 2%, about 0.2% to about 1.9%, about 0.2% to about 1.8%, about 0.2% to about 1.7%, about 0.2% to about 1.6%, about 0.2% to about 1.5%, about 0.2% to about 1.4%, about 0.2% to about 1.3%, about 0.2% to about 1.2%, about 0.2% to about 1.1%, about 0.2% to about 1%, about 0.2% to about 0.9%, about 0.2% to about 0.8%, about 0.2% to about 0.7%, about 0.2% to about 0.6%, about 0.2% to about 0.5%, about 0.3% to about 5%, about 0.3% to about 4%, about 0.3% to about 3%, about 0.3% to about 2%, about 0.3% to about 1.9%, about 0.3% to about 1.8%, about 0.3% to about 1.7%, about 0.3% to about 1.6%, about 0.3% to about 1.5%, about 0.3% to about 1.4%, about 0.3% to about 1.3%, about 0.3% to about 1.2%, about 0.3% to about 1.1%, about 0.3% to about 1%, about 0.3% to about 0.9%, about 0.3% to about 0.8%, about 0.3% to about 0.7%, about 0.3% to about 0.6%, about 0.3% to about 0.5%, about 0.4% to about 5%, about 0.4% to about 4%, about 0.4% to about 3%, about 0.4% to about 2%, about 0.4% to about 1.9%, about 0.4% to about 1.8%, about 0.4% to about 1.7%, about 0.4% to about 1.6%, about 0.4% to about 1.5%, about 0.4% to about 1.4%, about 0.4% to about 1.3%, about 0.4% to about 1.2%, about 0.4% to about 1.1%, about 0.4% to about 1%, about 0.4% to about 0.9%, about 0.4% to about 0.8%, about 0.4% to about 0.7%, about 0.4% to about 0.6%, about 0.4% to about 0.5%, about 0.5% to about 5%, about 0.5% to about 4%, about 0.5% to about 3%, about 0.5% to about 2%, about 0.5% to about 1.9%, about 0.5% to about 1.8%, about 0.5% to about 1.7%, about 0.5% to about 1.6%, about 0.5% to about 1.5%, about 0.5% to about 1.4%, about 0.5% to about 1.3%, about 0.5% to about 1.2%, about 0.5% to about 1.1%, about 0.5% to about 1%, about 0.5% to about 0.9%, about 0.5% to about 0.8%, about 0.5% to about 0.7%, about 0.5% to about 0.6%, about 0.6% to about 5%, about 0.6% to about 4%, about 0.6% to about 3%, about 0.6% to about 2%, about 0.6% to about 1.9%, about 0.6% to about 1.8%, about 0.6% to about 1.7%, about 0.6% to about 1.6%, about 0.6% to about 1.5%, about 0.6% to about 1.4%, about 0.6% to about 1.3%, about 0.6% to about 1.2%, about 0.6% to about 1.1%, about 0.6% to about 1%, about 0.6% to about 0.9%, about 0.6% to about 0.8%, about 0.6% to about 0.7%, about 0.7% to about 5%, about 0.7% to about 4%, about 0.7% to about 3%, about 0.7% to about 2%, about 0.7% to about 1.9%, about 0.7% to about 1.8%, about 0.7% to about 1.7%, about 0.7% to about 1.6%, about 0.7% to about 1.5%, about 0.7% to about 1.4%, about 0.7% to about 1.3%, about 0.7% to about 1.2%, about 0.7% to about 1.1%, about 0.7% to about 1%, about 0.7% to about 0.9%, about 0.7% to about 0.8%, about 0.8% to about 5%, about 0.8% to about 4%, about 0.8% to about 3%, about 0.8% to about 2%, about 0.8% to about 1.9%, about 0.8% to about 1.8%, about 0.8% to about 1.7%, about 0.8% to about 1.6%, about 0.8% to about 1.5%, about 0.8% to about 1.4%, about 0.8% to about 1.3%, about 0.8% to about 1.2%, about 0.8% to about 1.1%, about 0.8% to about 1%, about 0.8% to about 0.9%, about 0.9% to about 5%, about 0.9% to about 4%, about 0.9% to about 3%, about 0.9% to about 2%, about 0.9% to about 1.9%, about 0.9% to about 1.8%, about 0.9% to about 1.7%, about 0.9% to about 1.6%, about 0.9% to about 1.5%, about 0.9% to about 1.4%, about 0.9% to about 1.3%, about 0.9% to about 1.2%, about 0.9% to about 1.1%, about 0.9% to about 1%, about 1% to about 5%, about 1% to about 4%, about 1% to about 3%, about 1% to about 2%, about 1% to about 1.9%, about 1% to about 1.8%, about 1% to about 1.7%, about 1% to about 1.6%, about 1% to about 1.5%, about 1% to about 1.4%, about 1% to about 1.3%, about 1% to about 1.2%, about 1% to about 1.1%, about 1.1% to about 5%, about 1.1% to about 4%, about 1.1% to about 3%, about 1.1% to about 2%, about 1.1% to about 1.9%, about 1.1% to about 1.8%, about 1.1% to about 1.7%, about 1.1% to about 1.6%, about 1.1% to about 1.5%, about 1.1% to about 1.4%, about 1.1% to about 1.3%, about 1.1% to about 1.2%, about 1.2% to about 5%, about 1.2% to about 4%, about 1.2% to about 3%, about 1.2% to about 2%, about 1.2% to about 1.9%, about 1.2% to about 1.8%, about 1.2% to about 1.7%, about 1.2% to about 1.6%, about 1.2% to about 1.5%, about 1.2% to about 1.4%, about 1.2% to about 1.3%, about 1.3% to about 5%, about 1.3% to about 4%, about 1.3% to about 3%, about 1.3% to about 2%, about 1.3% to about 1.9%, about 1.3% to about 1.8%, about 1.3% to about 1.7%, about 1.3% to about 1.6%, about 1.3% to about 1.5%, about 1.3% to about 1.4%, about 1.4% to about 5%, about 1.4% to about 4%, about 1.4% to about 3%, about 1.4% to about 2%, about 1.4% to about 1.9%, about 1.4% to about 1.8%, about 1.4% to about 1.7%, about 1.4% to about 1.6%, about 1.4% to about 1.5%, about 1.5% to about 5%, about 1.5% to about 4%, about 1.5% to about 3%, about 1.5% to about 2%, about 1.5% to about 1.9%, about 1.5% to about 1.8%, about 1.5% to about 1.7%, or about 1.5% to about 1.6%.

In some embodiments, the composition further comprises at least one fragrance. Suitable fragrances are known to those of ordinary skill in the art. Additional additives may be needed to aid solubilizing the fragrance in the composition, as could readily be determined by one of ordinary skill in cosmetic or pharmaceutical formulations.

The composition may comprise an acid such as hydrochloric acid or a base such as NaCl to aid solubilizing, especially in synephrine formulations including glycolic acid.

The composition may comprise one or more antioxidants and preservatives in place of or in addition to the additives discussed above that act as preservatives, such as without limitation tetrasodium EDTA, sodium metabisulfite, and butylated hydroxytoluene (BHT). The amount of each antioxidant or preservative in the present compositions based on the total weight of the composition is about 0.01% to about 5%, about 0.01% to about 4%, about 0.01% to about 3%, about 0.01% to about 2%, about 0.01% to about 1%, about 0.01% to about 0.9%, about 0.01% to about 0.8%, about 0.01% to about 0.7%, about 0.01% to about 0.6%, about 0.01% to about 0.5%, about 0.01% to about 0.4%, about 0.01% to about 0.3%, about 0.01% to about 0.2%, about 0.01% to about 0.1%, about 0.03% to about 5%, about 0.03% to about 4%, about 0.03% to about 3%, about 0.03% to about 2%, about 0.03% to about 1%, about 0.03% to about 0.9%, about 0.03% to about 0.8%, about 0.03% to about 0.7%, about 0.03% to about 0.6%, about 0.03% to about 0.5%, about 0.03% to about 0.4%, about 0.03% to about 0.3%, about 0.03% to about 0.2%, about 0.03% to about 0.1%, about 0.04% to about 5%, about 0.04% to about 4%, about 0.04% to about 3%, about 0.04% to about 2%, about 0.04% to about 1%, about 0.04% to about 0.9%, about 0.04% to about 0.8%, about 0.04% to about 0.7%, about 0.04% to about 0.6%, about 0.04% to about 0.5%, about 0.04% to about 0.4%, about 0.04% to about 0.3%, about 0.04% to about 0.2%, about 0.04% to about 0.1%, about 0.05% to about 5%, about 0.05% to about 4%, about 0.05% to about 3%, about 0.05% to about 2%, about 0.05% to about 1%, about 0.05% to about 0.9%, about 0.05% to about 0.8%, about 0.05% to about 0.7%, about 0.05% to about 0.6%, about 0.05% to about 0.5%, about 0.05% to about 0.4%, about 0.05% to about 0.3%, about 0.05% to about 0.2%, about 0.05% to about 0.1%, about 0.06% to about 5%, about 0.06% to about 4%, about 0.06% to about 3%, about 0.06% to about 2%, about 0.06% to about 1%, about 0.06% to about 0.9%, about 0.06% to about 0.8%, about 0.06% to about 0.7%, about 0.06% to about 0.6%, about 0.06% to about 0.5%, about 0.06% to about 0.4%, about 0.06% to about 0.3%, about 0.06% to about 0.2%, about 0.06% to about 0.1%, about 0.07% to about 5%, about 0.07% to about 4%, about 0.07% to about 3%, about 0.07% to about 2%, about 0.07% to about 1%, about 0.07% to about 0.9%, about 0.07% to about 0.8%, about 0.07% to about 0.7%, about 0.07% to about 0.6%, about 0.07% to about 0.5%, about 0.07% to about 0.4%, about 0.07% to about 0.3%, about 0.07% to about 0.2%, about 0.07% to about 0.1%, about 0.08% to about 5%, about 0.08% to about 4%, about 0.08% to about 3%, about 0.08% to about 2%, about 0.08% to about 1%, about 0.08% to about 0.9%, about 0.08% to about 0.8%, about 0.08% to about 0.7%, about 0.08% to about 0.6%, about 0.08% to about 0.5%, about 0.08% to about 0.4%, about 0.08% to about 0.3%, about 0.08% to about 0.2%, about 0.08% to about 0.1%, about 0.09% to about 5%, about 0.09% to about 4%, about 0.09% to about 3%, about 0.09% to about 2%, about 0.09% to about 1%, about 0.09% to about 0.9%, about 0.09% to about 0.8%, about 0.09% to about 0.7%, about 0.09% to about 0.6%, about 0.09% to about 0.5%, about 0.09% to about 0.4%, about 0.09% to about 0.3%, about 0.09% to about 0.2%, about 0.09% to about 0.1%, about 0.1% to about 5%, about 0.1% to about 4%, about 0.1% to about 3%, about 0.1% to about 2%, about 0.1% to about 1.5%, about 0.1% to about 1%, about 0.1% to about 0.9%, about 0.8% to about 0.7%, about 0.1% to about 0.6%, about 0.1% to about 0.5%, about 0.1% to about 0.4%, about 0.1% to about 0.3%, about 0.1% to about 0.2%, about 0.2% to about 5%, about 0.2% to about 4%, about 0.2% to about 3%, about 0.2% to about 2%, about 0.2% to about 1.5%, about 0.2% to about 1%, about 0.2% to about 0.9%, about 0.8% to about 0.7%, about 0.2% to about 0.6%, about 0.2% to about 0.5%, about 0.2% to about 0.4%, about 0.2% to about 0.3%, about 0.3% to about 5%, about 0.3% to about 4%, about 0.3% to about 3%, about 0.3% to about 2%, about 0.3% to about 1.5%, about 0.3% to about 1%, about 0.3% to about 0.9%, about 0.8% to about 0.7%, about 0.3% to about 0.6%, about 0.3% to about 0.5%, about 0.3% to about 0.4%, about 0.4% to about 5%, about 0.4% to about 4%, about 0.4% to about 3%, about 0.4% to about 2%, about 0.4% to about 1.5%, about 0.4% to about 1%, about 0.4% to about 0.9%, about 0.8% to about 0.7%, about 0.4% to about 0.6%, or about 0.4% to about 0.5%.

The composition may comprise one or more moisturizers (also known as humectants), such as without limitation panthenol. A moisturizer may be present in the composition at a weight percentage based on the total weight of the composition of about 0.01% to about 5%, about 0.01% to about 4%, about 0.01% to about 3%, about 0.01% to about 2%, about 0.01% to about 1%, about 0.01% to about 0.9%, about 0.01% to about 0.8%, about 0.01% to about 0.7%, about 0.01% to about 0.6%, about 0.01% to about 0.5%, about 0.01% to about 0.4%, about 0.01% to about 0.3%, about 0.01% to about 0.2%, about 0.01% to about 0.1%, about 0.03% to about 5%, about 0.03% to about 4%, about 0.03% to about 3%, about 0.03% to about 2%, about 0.03% to about 1%, about 0.03% to about 0.9%, about 0.03% to about 0.8%, about 0.03% to about 0.7%, about 0.03% to about 0.6%, about 0.03% to about 0.5%, about 0.03% to about 0.4%, about 0.03% to about 0.3%, about 0.03% to about 0.2%, about 0.03% to about 0.1%, about 0.04% to about 5%, about 0.04% to about 4%, about 0.04% to about 3%, about 0.04% to about 2%, about 0.04% to about 1%, about 0.04% to about 0.9%, about 0.04% to about 0.8%, about 0.04% to about 0.7%, about 0.04% to about 0.6%, about 0.04% to about 0.5%, about 0.04% to about 0.4%, about 0.04% to about 0.3%, about 0.04% to about 0.2%, about 0.04% to about 0.1%, about 0.05% to about 5%, about 0.05% to about 4%, about 0.05% to about 3%, about 0.05% to about 2%, about 0.05% to about 1%, about 0.05% to about 0.9%, about 0.05% to about 0.8%, about 0.05% to about 0.7%, about 0.05% to about 0.6%, about 0.05% to about 0.5%, about 0.05% to about 0.4%, about 0.05% to about 0.3%, about 0.05% to about 0.2%, about 0.05% to about 0.1%, about 0.06% to about 5%, about 0.06% to about 4%, about 0.06% to about 3%, about 0.06% to about 2%, about 0.06% to about 1%, about 0.06% to about 0.9%, about 0.06% to about 0.8%, about 0.06% to about 0.7%, about 0.06% to about 0.6%, about 0.06% to about 0.5%, about 0.06% to about 0.4%, about 0.06% to about 0.3%, about 0.06% to about 0.2%, about 0.06% to about 0.1%, about 0.07% to about 5%, about 0.07% to about 4%, about 0.07% to about 3%, about 0.07% to about 2%, about 0.07% to about 1%, about 0.07% to about 0.9%, about 0.07% to about 0.8%, about 0.07% to about 0.7%, about 0.07% to about 0.6%, about 0.07% to about 0.5%, about 0.07% to about 0.4%, about 0.07% to about 0.3%, about 0.07% to about 0.2%, about 0.07% to about 0.1%, about 0.08% to about 5%, about 0.08% to about 4%, about 0.08% to about 3%, about 0.08% to about 2%, about 0.08% to about 1%, about 0.08% to about 0.9%, about 0.08% to about 0.8%, about 0.08% to about 0.7%, about 0.08% to about 0.6%, about 0.08% to about 0.5%, about 0.08% to about 0.4%, about 0.08% to about 0.3%, about 0.08% to about 0.2%, about 0.08% to about 0.1%, about 0.09% to about 5%, about 0.09% to about 4%, about 0.09% to about 3%, about 0.09% to about 2%, about 0.09% to about 1%, about 0.09% to about 0.9%, about 0.09% to about 0.8%, about 0.09% to about 0.7%, about 0.09% to about 0.6%, about 0.09% to about 0.5%, about 0.09% to about 0.4%, about 0.09% to about 0.3%, about 0.09% to about 0.2%, about 0.09% to about 0.1%, about 0.1% to about 5%, about 0.1% to about 4%, about 0.1% to about 3%, about 0.1% to about 2%, about 0.1% to about 1.5%, about 0.1% to about 1%, about 0.1% to about 0.9%, about 0.8% to about 0.7%, about 0.1% to about 0.6%, about 0.1% to about 0.5%, about 0.1% to about 0.4%, about 0.1% to about 0.3%, about 0.1% to about 0.2%, about 0.2% to about 5%, about 0.2% to about 4%, about 0.2% to about 3%, about 0.2% to about 2%, about 0.2% to about 1.5%, about 0.2% to about 1%, about 0.2% to about 0.9%, about 0.8% to about 0.7%, about 0.2% to about 0.6%, about 0.2% to about 0.5%, about 0.2% to about 0.4%, about 0.2% to about 0.3%, about 0.3% to about 5%, about 0.3% to about 4%, about 0.3% to about 3%, about 0.3% to about 2%, about 0.3% to about 1.5%, about 0.3% to about 1%, about 0.3% to about 0.9%, about 0.8% to about 0.7%, about 0.3% to about 0.6%, about 0.3% to about 0.5%, about 0.3% to about 0.4%, about 0.4% to about 5%, about 0.4% to about 4%, about 0.4% to about 3%, about 0.4% to about 2%, about 0.4% to about 1.5%, about 0.4% to about 1%, about 0.4% to about 0.9%, about 0.8% to about 0.7%, about 0.4% to about 0.6%, or about 0.4% to about 0.5%.

The composition further may comprise niacinamide, which is a known additive in hair care products. Niacinamide may be present in the composition at a weight percentage based on the total weight of the composition of about 0.01% to about 5%, about 0.01% to about 4%, about 0.01% to about 3%, about 0.01% to about 2%, about 0.01% to about 1%, about 0.01% to about 0.9%, about 0.01% to about 0.8%, about 0.01% to about 0.7%, about 0.01% to about 0.6%, about 0.01% to about 0.5%, about 0.01% to about 0.4%, about 0.01% to about 0.3%, about 0.01% to about 0.2%, about 0.01% to about 0.1%, about 0.03% to about 5%, about 0.03% to about 4%, about 0.03% to about 3%, about 0.03% to about 2%, about 0.03% to about 1%, about 0.03% to about 0.9%, about 0.03% to about 0.8%, about 0.03% to about 0.7%, about 0.03% to about 0.6%, about 0.03% to about 0.5%, about 0.03% to about 0.4%, about 0.03% to about 0.3%, about 0.03% to about 0.2%, about 0.03% to about 0.1%, about 0.04% to about 5%, about 0.04% to about 4%, about 0.04% to about 3%, about 0.04% to about 2%, about 0.04% to about 1%, about 0.04% to about 0.9%, about 0.04% to about 0.8%, about 0.04% to about 0.7%, about 0.04% to about 0.6%, about 0.04% to about 0.5%, about 0.04% to about 0.4%, about 0.04% to about 0.3%, about 0.04% to about 0.2%, about 0.04% to about 0.1%, about 0.05% to about 5%, about 0.05% to about 4%, about 0.05% to about 3%, about 0.05% to about 2%, about 0.05% to about 1%, about 0.05% to about 0.9%, about 0.05% to about 0.8%, about 0.05% to about 0.7%, about 0.05% to about 0.6%, about 0.05% to about 0.5%, about 0.05% to about 0.4%, about 0.05% to about 0.3%, about 0.05% to about 0.2%, about 0.05% to about 0.1%, about 0.06% to about 5%, about 0.06% to about 4%, about 0.06% to about 3%, about 0.06% to about 2%, about 0.06% to about 1%, about 0.06% to about 0.9%, about 0.06% to about 0.8%, about 0.06% to about 0.7%, about 0.06% to about 0.6%, about 0.06% to about 0.5%, about 0.06% to about 0.4%, about 0.06% to about 0.3%, about 0.06% to about 0.2%, about 0.06% to about 0.1%, about 0.07% to about 5%, about 0.07% to about 4%, about 0.07% to about 3%, about 0.07% to about 2%, about 0.07% to about 1%, about 0.07% to about 0.9%, about 0.07% to about 0.8%, about 0.07% to about 0.7%, about 0.07% to about 0.6%, about 0.07% to about 0.5%, about 0.07% to about 0.4%, about 0.07% to about 0.3%, about 0.07% to about 0.2%, about 0.07% to about 0.1%, about 0.08% to about 5%, about 0.08% to about 4%, about 0.08% to about 3%, about 0.08% to about 2%, about 0.08% to about 1%, about 0.08% to about 0.9%, about 0.08% to about 0.8%, about 0.08% to about 0.7%, about 0.08% to about 0.6%, about 0.08% to about 0.5%, about 0.08% to about 0.4%, about 0.08% to about 0.3%, about 0.08% to about 0.2%, about 0.08% to about 0.1%, about 0.09% to about 5%, about 0.09% to about 4%, about 0.09% to about 3%, about 0.09% to about 2%, about 0.09% to about 1%, about 0.09% to about 0.9%, about 0.09% to about 0.8%, about 0.09% to about 0.7%, about 0.09% to about 0.6%, about 0.09% to about 0.5%, about 0.09% to about 0.4%, about 0.09% to about 0.3%, about 0.09% to about 0.2%, about 0.09% to about 0.1%, about 0.1% to about 5%, about 0.1% to about 4%, about 0.1% to about 3%, about 0.1% to about 2%, about 0.1% to about 1.5%, about 0.1% to about 1%, about 0.1% to about 0.9%, about 0.8% to about 0.7%, about 0.1% to about 0.6%, about 0.1% to about 0.5%, about 0.1% to about 0.4%, about 0.1% to about 0.3%, about 0.1% to about 0.2%, about 0.2% to about 5%, about 0.2% to about 4%, about 0.2% to about 3%, about 0.2% to about 2%, about 0.2% to about 1.5%, about 0.2% to about 1%, about 0.2% to about 0.9%, about 0.8% to about 0.7%, about 0.2% to about 0.6%, about 0.2% to about 0.5%, about 0.2% to about 0.4%, or about 0.2% to about 0.3%.

Surfactants and emulsifiers may also be present in the compositions, including without limitation polysorbate 80 (also known as TWEEN 80). A surfactant or emulsifier may function to solubilize additives, such as the fragrance. One or more surfactants or emulsifiers may be present in the composition at a weight percentage for each emulsifier or surfactant based on the total weight of the composition of about 0.01% to about 5%, about 0.01% to about 4%, about 0.01% to about 3%, about 0.01% to about 2%, about 0.01% to about 1%, about 0.01% to about 0.9%, about 0.01% to about 0.8%, about 0.01% to about 0.7%, about 0.01% to about 0.6%, about 0.01% to about 0.5%, about 0.01% to about 0.4%, about 0.01% to about 0.3%, about 0.01% to about 0.2%, about 0.01% to about 0.1%, about 0.03% to about 5%, about 0.03% to about 4%, about 0.03% to about 3%, about 0.03% to about 2%, about 0.03% to about 1%, about 0.03% to about 0.9%, about 0.03% to about 0.8%, about 0.03% to about 0.7%, about 0.03% to about 0.6%, about 0.03% to about 0.5%, about 0.03% to about 0.4%, about 0.03% to about 0.3%, about 0.03% to about 0.2%, about 0.03% to about 0.1%, about 0.04% to about 5%, about 0.04% to about 4%, about 0.04% to about 3%, about 0.04% to about 2%, about 0.04% to about 1%, about 0.04% to about 0.9%, about 0.04% to about 0.8%, about 0.04% to about 0.7%, about 0.04% to about 0.6%, about 0.04% to about 0.5%, about 0.04% to about 0.4%, about 0.04% to about 0.3%, about 0.04% to about 0.2%, about 0.04% to about 0.1%, about 0.05% to about 5%, about 0.05% to about 4%, about 0.05% to about 3%, about 0.05% to about 2%, about 0.05% to about 1%, about 0.05% to about 0.9%, about 0.05% to about 0.8%, about 0.05% to about 0.7%, about 0.05% to about 0.6%, about 0.05% to about 0.5%, about 0.05% to about 0.4%, about 0.05% to about 0.3%, about 0.05% to about 0.2%, about 0.05% to about 0.1%, about 0.06% to about 5%, about 0.06% to about 4%, about 0.06% to about 3%, about 0.06% to about 2%, about 0.06% to about 1%, about 0.06% to about 0.9%, about 0.06% to about 0.8%, about 0.06% to about 0.7%, about 0.06% to about 0.6%, about 0.06% to about 0.5%, about 0.06% to about 0.4%, about 0.06% to about 0.3%, about 0.06% to about 0.2%, about 0.06% to about 0.1%, about 0.07% to about 5%, about 0.07% to about 4%, about 0.07% to about 3%, about 0.07% to about 2%, about 0.07% to about 1%, about 0.07% to about 0.9%, about 0.07% to about 0.8%, about 0.07% to about 0.7%, about 0.07% to about 0.6%, about 0.07% to about 0.5%, about 0.07% to about 0.4%, about 0.07% to about 0.3%, about 0.07% to about 0.2%, about 0.07% to about 0.1%, about 0.08% to about 5%, about 0.08% to about 4%, about 0.08% to about 3%, about 0.08% to about 2%, about 0.08% to about 1%, about 0.08% to about 0.9%, about 0.08% to about 0.8%, about 0.08% to about 0.7%, about 0.08% to about 0.6%, about 0.08% to about 0.5%, about 0.08% to about 0.4%, about 0.08% to about 0.3%, about 0.08% to about 0.2%, about 0.08% to about 0.1%, about 0.09% to about 5%, about 0.09% to about 4%, about 0.09% to about 3%, about 0.09% to about 2%, about 0.09% to about 1%, about 0.09% to about 0.9%, about 0.09% to about 0.8%, about 0.09% to about 0.7%, about 0.09% to about 0.6%, about 0.09% to about 0.5%, about 0.09% to about 0.4%, about 0.09% to about 0.3%, about 0.09% to about 0.2%, about 0.09% to about 0.1%, about 0.1% to about 5%, about 0.1% to about 4%, about 0.1% to about 3%, about 0.1% to about 2%, about 0.1% to about 1.5%, about 0.1% to about 1%, about 0.1% to about 0.9%, about 0.8% to about 0.7%, about 0.1% to about 0.6%, about 0.1% to about 0.5%, about 0.1% to about 0.4%, about 0.1% to about 0.3%, about 0.1% to about 0.2%, about 0.2% to about 5%, about 0.2% to about 4%, about 0.2% to about 3%, about 0.2% to about 2%, about 0.2% to about 1.5%, about 0.2% to about 1%, about 0.2% to about 0.9%, about 0.8% to about 0.7%, about 0.2% to about 0.6%, about 0.2% to about 0.5%, about 0.2% to about 0.4%, or about 0.2% to about 0.3%.

Exemplary Compositions

In some embodiments, the composition comprises water, synephrine, PEG-6 caprylic/capric glycerides, propanediol, phenoxyethanol, sodium metabisulfite, panthenol, niacinamide, butylated hydroxytoluene, polysorbate 80, phenoxyethanol and tetrasodium EDTA (ethylenediamenetraacetic acid tetrasodium salt). In one or more embodiments, the composition further comprises a fragrance.

In some embodiments, the composition consists essentially of water, synephrine, PEG-6 caprylic/capric glycerides, propanediol, phenoxyethanol, sodium metabisulfite, panthenol, niacinamide, butylated hydroxytoluene, polysorbate 80, phenoxyethanol and tetrasodium EDTA (ethyl enediamenetraacetic acid tetrasodium salt) and fragrance.

In some embodiments, the composition consists of water, synephrine, PEG-6 caprylic/capric glycerides, propanediol, phenoxyethanol, sodium metabisulfite, panthenol, niacinamide, butylated hydroxytoluene, polysorbate 80, phenoxyethanol and tetrasodium EDTA (ethylenediamenetraacetic acid tetrasodium salt) and fragrance. In other embodiments, the composition consists of water, synephrine, PEG-6 caprylic/capric glycerides, glycolic acid, at least one fragrance, propanediol, phenoxyethanol, sodium metabisulfite, panthenol, niacinamide, ethylhexylgylcerin, butylated hydroxytoluene, and tetrasodium EDTA (ethyl enediamenetraacetic acid tetrasodium salt).

An example of one particular composition according to the present invention is a composition comprising about 10% to about 60% by weight of synephrine and about 5% to about 40% by weight of PEG-6 caprylic/capric glycerides. In some embodiments, the composition comprises about 30% to about 60% by weight of water, about 25% to about 45% by weight of synephrine, and about 5% to about 40% by weight of PEG-6 caprylic/capric glycerides. In some embodiments, the composition comprises about 40% to about 60% by weight of water, about 30% to about 50% by weight of synephrine, and about 8% to about 12% by weight of PEG-6 caprylic/capric glycerides.

In another example of a particular composition according to the present invention, the composition comprises about 30% to about 60% by weight of water, about 30% to about 45% by weight of synephrine, about 10% to about 20% by weight of glycolic acid, about 5% to about 15% by weight of PEG-6 caprylic/capric glycerides, about 4% to about 12% by weight of hydrochloric acid, about 1% to about 5% by weight of propanediol, about 0.4% to about 3% by weight of phenoxyethanol, about 0.1% to about 0.5% by weight of sodium metabisulfite, about 0.02% to about 0.5% by weight of panthenol, about 0.02% to about 0.5% by weight of niacinamide, about 0.04% to about 0.3% ethylhexylgylcerin, about 0.02% to about 0.5% by weight of butylated hydroxytoluene, and about 0.02% to about 0.5% by weight of tetrasodium EDTA (ethylenediamenetraacetic acid tetrasodium salt). In one or more embodiments, the composition may further comprise about 0.1% to about 2% by weight of a fragrance.

In yet another example of a particular composition according to the present invention, the composition comprises about 30% to about 50% by weight of water, about 28% to about 42% by weight of synephrine, about 8% to about 12% by weight of PEG-6 caprylic/capric glycerides, about 2% to about 4% by weight of propanediol, about 0.7% to about 1.1% by weight of phenoxyethanol ethylhexylglycerin, about 0.1% to about 0.5% by weight of sodium metabisulfite, about 0.01% to about 0.15% by weight of panthenol, about 0.01% to about 0.15% by weight of niacinamide, about 0.1% to about 2.0% phenoxyethanol ethylhexylgylcerin, about 0.05% to about 0.15% by weight of butylated hydroxytoluene, and about 0.05% to about 0.15% by weight of tetrasodium EDTA. In one or more embodiments, the composition may further comprise about 0.2% to about 0.8% by weight of a fragrance.

In an exemplary embodiment, the composition may comprise about 40-50% by weight of water, about 30-40% by weight of synephrine, and about 8-10% by weight of Acconon® CC-6 (PEG-6 caprylic/capric glycerides). The composition further may comprise about 3% by weight of propanediol, about 0.9% by weight of phenoxyethanol ethylhexylglycerin, about 0.5% by weight of a fragrance, about 0.3% by weight of sodium metabisulfite, about 0.1% by weight of panthenol, about 0.05% by weight of niacinamide, about 1.0% by weight of phenoxyethanol ethylhexylgylcerin, about 0.1% by weight of butylated hydroxytoluene, and about 0.1% by weight of tetrasodium EDTA (ethylenediamenetraacetic acid tetrasodium salt).

In some embodiments, the composition comprises water, synephrine, PEG-6 caprylic/capric glycerides, propanediol, phenoxyethanol ethylhexylgylcerin, one or more preservatives and one or more humectants. In one or more embodiments, the composition may further comprise a fragrance.

In some embodiments, the composition comprises water, R-(−)-synephrine, PEG-6 caprylic/capric glycerides, propanediol, phenoxyethanol, sodium metabisulfite, panthenol, niacinamide, phenoxyethanol ethylhexylgylcerin, butylated hydroxytoluene, and tetrasodium EDTA (ethylenediamenetraacetic acid tetrasodium salt). In one or more embodiments, the composition may further comprise a fragrance.

In some embodiments, the composition comprises water, R-(−)-synephrine, S-(+)-synephrine, PEG-6 caprylic/capric glycerides, propanediol, phenoxyethanol, sodium metabisulfite, panthenol, niacinamide, phenoxyethanol ethylhexylgylcerin, butylated hydroxytoluene, and tetrasodium EDTA (ethylenediamenetraacetic acid tetrasodium salt). In one or more embodiments, the composition may further comprise a fragrance and a surfactant, such as Tween 80, to aid in solubilizing the fragrance.

An example of one particular composition according to the present invention is a composition comprising about 30% to about 50% by weight of water, about 40% to about 70% by weight of synthetically produced synephrine, and about 5% to about 60% by weight of PEG-6 caprylic/capric glycerides. In some embodiments, the composition comprises about 40% to about 60% by weight of water, about 30% to about 60% by weight of synephrine HCl, and about 8% to about 20% by weight of PEG-6 caprylic/capric glycerides.

In some embodiments, the composition consists essentially of water, synephrine, PEG-6 caprylic/capric glycerides, at least one fragrance, propanediol, phenoxyethanol ethylhexylgylcerin, sodium metabisulfite, panthenol, niacinamide, and one or more preservatives such as without limitation butylated hydroxytoluene and tetrasodium EDTA (ethylenediamenetraacetic acid tetrasodium salt).

In some embodiments, the composition consists of water, synephrine, glycolic acid, PEG-6 caprylic/capric glycerides, hydrochloric acid, at least one fragrance, propanediol, phenoxyethanol, sodium metabisulfite, panthenol, niacinamide, ethylhexylgylcerin, butylated hydroxytoluene, and tetrasodium EDTA (ethylenediamenetraacetic acid tetrasodium salt).

Compositions Comprising Less Penetration Enhancer

In some embodiments, the composition comprises less penetration enhancer than the compositions discussed above. In such embodiments, the amount of synephrine is increased to accommodate the reduced penetration efficacy.

An example of one particular composition according to the present invention is a composition comprising about 20% to about 40% by weight of water, about 40% to about 60% by weight of synephrine, and about 3% to about 10% by weight of a penetration enhancer such as PEG-6 caprylic/capric glycerides. In some embodiments, the composition comprises about 30% to about 35% by weight of water, about 45% to about 55% by weight of synephrine, and about 3% to about 8% by weight of one or more penetration enhancers such as PEG-6 caprylic/capric glycerides.

Methods of Use

The compositions comprising synephrine described herein may be used in methods of treating or preventing various conditions related to hair loss especially hair loss such as traction alopecia and also to reduce the shedding of hair while the hair is being washed, brushed, colored, styled, or otherwise stressed. In one embodiment, therapeutically effective amounts of the compositions described herein are applied topically to the scalp or other body surface containing hair follicles where prevention or treatment of hair loss is desired about 8 minutes to about 20 minutes prior to stress being applied, such as the stress of a tight ponytail, hair weave, etc. In further embodiments, the synephrine composition is applied about or at least 1, 2, 3, 4, 5, 6, 7, 8, 9, 10, 11, 12, 13, 14, 15, 16, 17, 18, 19, or 20 minutes before stress is applied to the hair, or from 1-5 minutes, 1-10 minutes, 1-15 minutes, 1-20 minutes, 1-30 minutes, 1-40 minutes, 1-50 minutes, 1-60 minutes, 5-10 minutes, 5-15 minutes, 5-20 minutes, 5-30 minutes, 5-40 minutes, 5-50 minutes, 5-60 minutes, 10-20 minutes, 10-30 minutes, 10-40 minutes, 10-50 minutes, 10-60 minutes, 20-30 minutes, 30-40 minutes, 40-60 minutes, or 30 to 90 minutes before stress is applied to the hair. In certain embodiments, a synephrine composition is applied twice or more to the scalp before the hair is subjected to stressing. The same or different composition may be applied when multiple applications are used. Preferably the synephrine composition is applied twice before subjecting the hair to a pulling stress. In one embodiment, the synephrine solution is applied as a prewashing solution twice 30 minutes before shampooing or applying hair color.

During or after the hair experiences stress, the compositions discussed above may be washed out, such as by shampooing. The compositions of the present disclosure are liquid solutions. The liquid solution may be applied directly to the scalp and rubbed into the scalp, or applied by spraying on with a delivery device such as a pump sprayer. The composition of the present disclosure may further be combined with a shampoo or a conditioner or other hair care product to create a product that has more than one function.

In some embodiments, the compositions described herein are provided as a kit. A "kit" typically defines a package including at least one composition of the invention and another item useful in its application, such as a comb, brush or other applicator, or with another hair care composition product, such as a shampoo, hair color/dye, hair oil or conditioner. For example, a kit may be a package containing at least one composition of the invention and a spray container or a dropper for administering the composition. In another embodiment, the kit is a package containing (1) the present composition and (2) one or more of a shampoo, hairspray, conditioner, detangling solution, hair color, henna, or hair oil (such as without limitation coconut oil, jojoba oil, olive oil, baby oil, and black castor oil) and optionally (3) a pump spray container holding the synephrine composition or suitable to hold the synephrine composition.

Manufacturing Synephrine Compositions

The technology described herein provides a method of manufacturing compositions comprising water, bitter orange extract, and a penetration enhancer. The technology described herein also provides a method of manufacturing compositions comprising water, synephrine, and a penetration enhancer.

The components may be grouped into phases to organize the manufacturing process.

In one embodiment, Phase A comprises water and synephrine, preferably synephrine HCl. Phase A may further comprise one or more preservatives, diol, niacinamide, and/or moisturizer such as panthenol. Phase B comprises a penetration enhancer. In some embodiments, Phase B comprises PEG-6 caprylic/capric glycerides. Phase B may further comprise a fragrance and other additives, such as polysorbate 80. In some embodiments, Phase B comprises PEG-6 caprylic/capric glycerides and a fragrance. Phase C may be absent, or may comprise a preservative such as BHT. Phase D comprises additives, such as diols and or preservatives like phenoxythanol ethylhexylglycerin.

In this embodiment, the manufacturing occurs by the following steps:

First, mix the components of Phase A together until uniformly dispersed or dissolved. The mixture will be referred to as the batch. Second, mix the components of Phase B together with heat until all material is added and uniformly dissolved/dispersed. Third, if Phase C is present, add phase C to B and mix until uniform. Fourth, add Phase D to the mixture of B and C and mix. Fifth, Mix the step 1 and step four solutions together with heat (30-50 degrees C.) until completely dissolved. Sixth, cool to room temperature, adjust pH to about 4.9 to 5.3 with NaOH or HCl and let sit, preferably for at least one day, and then filter using a coarse filter paper.

EXAMPLES

Example 1: Extracting and Purifying R-(−)-Synephrine from Bitter Orange Extract

R-(−)-Synephrine was extracted from *Citrus Aurantium* in a first stage, and purified in a second stage.

To washed raw *Citrus Aurantium* (*Citrus Aurantium* L.), alcohol was added and used to extract synephrine from the raw material. The purity of the alcohol used for extraction was at least 80%. The extraction was repeated three times for about 2 hours each. The extraction formed an extract solution.

The extract solution was concentrated under a vacuum pressure of −0.08 mpa at a temperature of 60° C. The concentrated solution formed a first extractum.

The first extractum was agitated and dissolved in ethanol. The ethanol had a purity of at least about 98% ethanol. The extractum dissolved in the ethanol formed a first solution.

The first solution was applied to resin and eluted. A disused mobile phase was discarded.

Next, the eluent was concentrated. Similar to the step discussed above, the eluent was concentrated under a vacuum pressure of −0.08 mpa at a temperature of 60° C. The concentrated solution formed a second extractum.

The second extractum was dissolved in a second solution. The second solution with the dissolved second extractum had a liquid specific gravity of about 1.08.

The second solution was spray dried. The dried product comprised about 30% by weight of R-(−)-synephrine. The dried product of about 30% by weight of R-(−)-synephrine was further purified in a second stage. Starting materials containing less than 30% synephrine may be used and isolated and purified using the above procedures to yield a purified product of lower concentration.

In the second stage, the dried product of about 30% by weight of R-(−)-synephrine was agitated and dissolved in ethanol. The ethanol was at least about 98% ethanol. R-(−)-synephrine was crystallized from alcohol for about 12 hours. The solid phase was vacuum dried to a purity of at least about 98% by weight of R-(−)-synephrine. Purity of synephrine was measured using HPLC. Enantiomer concentrations can be determined using circular dichroism.

Example 2—Alternative Second Stage

The steps were performed as in Example 1, except that in the second stage, the dried product of about 30% by weight of R-(−)-synephrine was agitated and dissolved in ethanol. The ethanol had a purity of at least about 98% ethanol. R-(−)-synephrine was crystallized from alcohol for about 12 hours. The solution phase passed through activated carbon for decoloration, producing a destaining solution. R-(−)-synephrine was crystallized from the destaining solution comprising alcohol for about 12 hours. The resulting crystal comprises at least about 95% by weight of R-(−)-synephrine.

Example 3—Composition of formula 00

TABLE 1

| Phase | Ingredient (Trade Name) | % by Weight | INCI Name |
| --- | --- | --- | --- |
| A | WATER | 32.95 | Water |
| A | HYDROCHLORIC ACID | 7.56 | Hydrochloric Acid |
| A | GLYCOLIC ACID (70% Solution) | 14.29 | Glycolic Acid |
| B | BITTER ORANGE EXTRACT | 30.00 | *Citrus Aurantium Amara* Extract |
| C | ACCONON CC-6 ® | 10.00 | PEG-6 Caprylic/Capric Glycerides |
| C | Fragrance | 0.50 | Fragrance |
| D | ZEMEA PROPANEDIOL | 3.00 | Propanediol |
| D | EUXYL PE 9010 (90%) | 0.90 | Phenoxyethanol |
| D | EUXYL PE 9010 (10%) | 0.10 | Ethylhexylglycerin |
| E | SODIUM METABISULFITE | 0.30 | Sodium Metabisulfite |
| E | dl PANTHENOL | 0.10 | Panthenol |
| E | NIACINAMIDE | 0.10 | Niacinamide |
| E | BUTYLATED HYDROXYTOLUENE | 0.10 | Butylated hydroxytoluene |
| E | TETRASODIUM EDTA | 0.10 | Tetrasodium EDTA |

The components were grouped into the phases listed in Table 1 above to organize the manufacturing process.

First, the components of Phase A were mixed together. The mixture was referred to as the batch.

Second, Phase B was slowly added to Phase A with mixing until all material was added and uniformly dissolved/dispersed in the batch. The pH was checked and adjusted to a pH of about 7.6. To adjust the pH, 5M NaOH was added to raise the pH or 5M HCL was added to lower the pH. The solution comprising Phase A and Phase B mixed together was clear or slightly hazy.

Third, the components of Phase C were mixed together. Next, Phase C was added to the batch and mixed until Phase C dissolved.

Fourth, the components of Phase D were mixed together. Next, Phase D was added to the batch and mixed until Phase D dissolved.

Fifth, each component of Phase E was added to the batch one at a time. The batch was mixed until uniform after the addition of each component in Phase E. The pH was checked and adjusted to a pH of about 7.6 by adding 5M NaOH to raise the pH or adding 5M HCL to lower the pH.

Sixth, the batch sat for at least 24 hours. After sitting, the batch was filtered through coarse filter paper.

Stability tests were performed on the composition of formula 00. Accelerated aging tests are useful in helping to determine expected formulation degradation over a long period of time by subjecting the product to elevated temperatures for a much shorter time period. Shelf-life data for a product can be extrapolated using the Arrhenius Equation, which relates chemical reaction rate (k) to absolute temperature (T). Samples of synephrine compositions are analyzed using a UV-visual spectrophotometer (Shamadzu, UV-1700). At least 5 separate serial dilutions are suggested to take the average of absorbance values. For synephrine, 273 nm is the wavelength chosen. Absorption data can be used to determine percent mass loss over time period tested. This data can be extrapolated to determine long-term stability of the sample.

The results of the accelerated aging tests are reported in the following table:

TABLE 2

| Day (room temperature equivalent) | Absolute intensity | % activity of synephrine |
| --- | --- | --- |
| 0 | 4279 | 100% |
| 37 | 3389 | 79% |
| 91 | 3312 | 77% |
| 128 | 3300 | 77% |

Example 4—Composition of Formula 01

TABLE 3

| Phase | Ingredient (Trade Name) | % by Weight | INCI Name |
| --- | --- | --- | --- |
| A | WATER | 47.15 | Water |
| A | TETRASODIUM EDTA | 0.10 | Tetrasodium EDTA |
| A | SODIUM METABISULFITE | 0.30 | sodium metabisulfite |
| A | SYNEPHRINE | 37.00 | P-synephrine HCl |
| A | dl PANTHENOL | 0.05 | Panthenol |
| A | NIACINAMIDE | 0.05 | Niacinamide |
| B | ACCONON CC-6 ® | 10.00 | PEG-6 Caprylic/Capric Glycerides |
| B | Fragrance | 0.25 | Fragrance |
| B | Polysorbate 80 | 1.00 | Polysorbate 80 |
| C | BHT | 0.10 | Butylated hydroxytoluene |
| D | ZEMEA PROPANEDIOL | 3.00 | 1,3-Propanediol |

TABLE 3-continued

| Phase | Ingredient (Trade Name) | % by Weight | INCI Name |
|---|---|---|---|
| D | EUXYL PE 9010 (90%) | 1.00 | Phenoxyethanol Ethylhexylglycerin |

To produce the composition of Example 4, the components were grouped into the phases listed in the table above. First, in step 1, the components of Phase A were mixed together until uniformly dispersed or dissolved. The mixture will be referred to as the batch. Second, the components of Phase B were mixed together with heat until all material is added and uniformly dissolved/dispersed. Third, phase C was added to B and mixed until uniform. Fourth, in step 4 Phase D was added to the mixture of B and C with mixing. Fifth, the step 1 and step four solutions were mixed together with heat (45 degrees C.) until completely dissolved. Sixth, the resulting mixture was cooled to room temperature, pH was adjusted to about 4.9 to 5.3 with NaOH or HCl and the product was allowed to sit for at least one day, before subjecting to filtration over coarse filter paper. The resulting product was stable as shown in the tests reported below.

Stability tests were performed on the composition of formula 01 following the procedure for accelerated aging tests described in Example 3. The results are reported in the following table:

TABLE 4

| Day (room temperature equivalent) | Absolute intensity | % activity of synephrine |
|---|---|---|
| 0 | 3566 | 100% |
| 78 | 3600 | 101% |
| 195 | 3635 | 102% |
| 286 | 3569 | 100% |
| 728 | 3905 | 110% |

A double blinded placebo controlled clinical study was conducted to assess the efficacy of the composition of Example 4 (referred to as formula 01) in reducing the amount of hair on a brush during hair brushing procedures. Fourteen healthy women volunteers ages 18-65 were recruited. A placebo solution (vehicle) was applied to one side of the scalp in an area of 8 cm×10 cm (investigative area 01). On the other side of the scalp formula 01 was applied in a similar area of 8 cm×10 cm (investigative area 02). The application process was 2 mL of the placebo or formula 01 applied directly to the scalp in the investigated region, rubbing of the investigated region followed by a second application of 2 mL of the placebo or formula 01 onto the investigated region. The second application used the same solution (placebo or formula 01) in the same region. Ten minutes after application, the investigative areas were washed. A clean brush was used to brush each investigative area 20 times. The number of hair on each brush was counted by an independent expert. In total 93% of subjects responded to formula 01. The maximum response was a reduction of 76% in hair shedding during styling and an average reduction of 44%. The data is reported in FIG. 1.

Example 5—Efficacy Data for Different Synephrine Concentrations

The controlled clinical study protocol discussed above for formula 01 (37% synephrine HCl) was performed with formula 02 (25% synephrine HCl) and with formula 03 (30% synephrine HCl). The clinical study with formula 02 demonstrated an average reduction in hair shedding of 4%. The clinical study with formula 03 demonstrated an average reduction in hair shedding of 29%. With formula 01 (37% synephrine HCl) the average reduction in hair shedding was demonstrated to be 44%. In addition, a modified protocol of a single application of each formula was performed. The modified protocol required washing after 30 minutes. A single application of formula 03 yielded a 25% reduction in hair shedding; however, when tested by washing 10 minutes after applying the composition the formula yielded 0.01% reduction in shedding. This data shows that multiple applications of the composition increases efficacy and time to response.

Example 6—Composition of formula 04

TABLE 5

| Ingredient (Trade Name) | % by Weight | INCI Name |
|---|---|---|
| WATER | 56.15 | Water |
| TETRASODIUM EDTA | 0.10 | Tetrasodium EDTA |
| SODIUM METABISULFITE | 0.30 | sodium metabisulfite |
| SYNEPHRINE | 37.00 | P-synephrine HCl |
| dl PANTHENOL | 0.05 | Panthenol |
| NIACINAMIDE | 0.05 | Niacinamide |
| Di(ethylene glycol) ethyl ether | 1.00 | Di(ethylene glycol) ethyl ether |
| Fragrance | 0.25 | Fragrance |
| Polysorbate 80 | 1.00 | Polysorbate 80 |
| BHT | 0.10 | Butylated hydroxytoluene |
| ZEMEA PROPANEDIOL | 3.00 | 1,3-Propanediol |
| EUXYL PE 9010 (90%) | 1.00 | Phenoxyethanol Ethylhexylglycerin |

The composition of Example 6 (formula 04) was prepared analogously to the composition of Example 4.

Example 7—In Vitro Study of Percutaneous Synephrine Permeation

Figure 2:
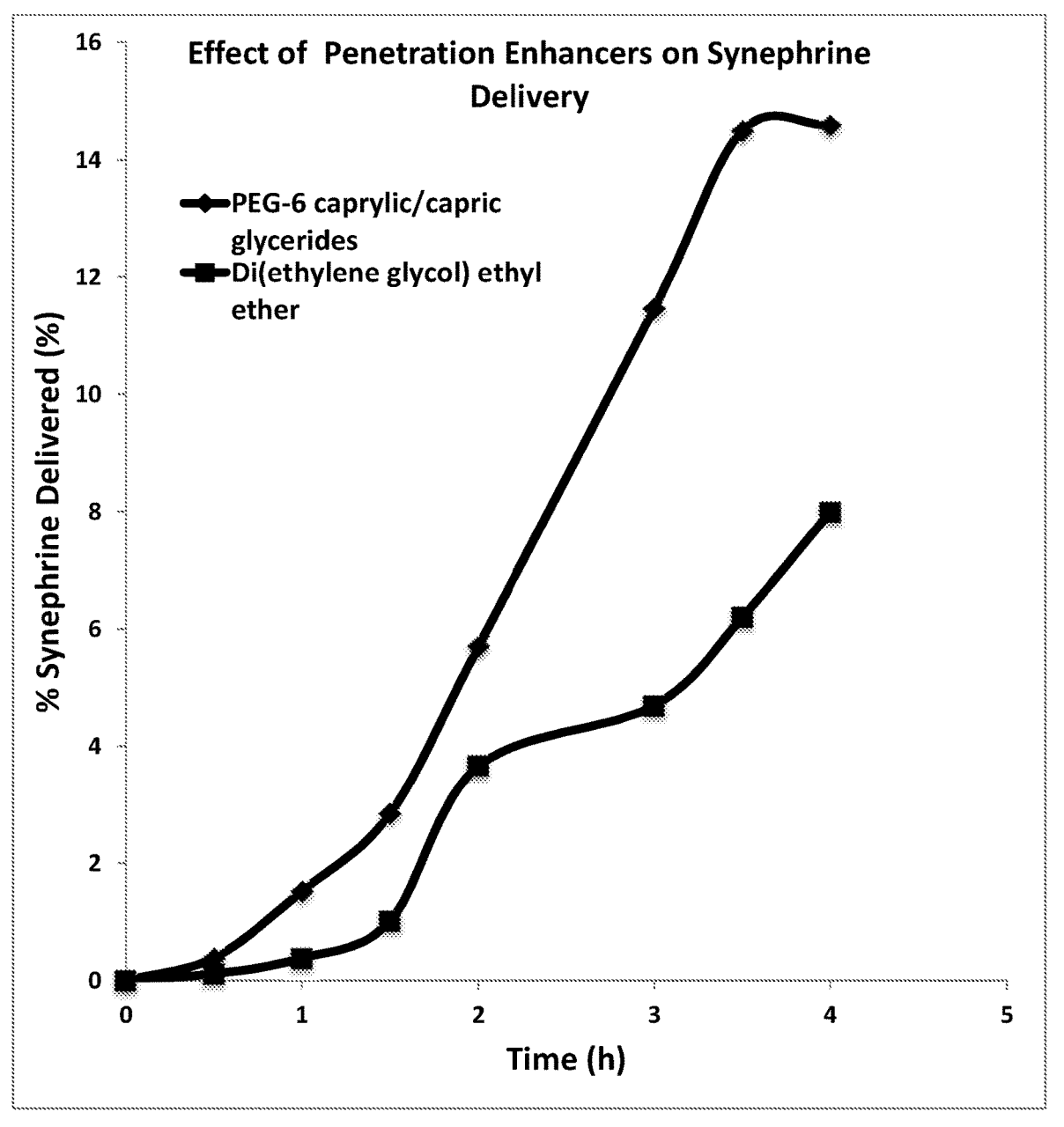

In vitro percutaneous synephrine permeation studies were performed on (1) the composition of formula 01, containing 37% synephrine and PEG-6 caprylic/capric glycerides and (2) the composition of formula 04, containing 37% synephrine and di(ethylene glycol) ethyl ether. The results are reported in FIG. 2. As can be seen from FIG. 2, the penetration of synephrine with an embodiment of the invention containing PEG-6 caprylic/capric glycerides as a penetration enhancer is superior to the penetration obtained from a composition containing the penetration enhancer di(ethylene glycol) ethyl ether.

The in vitro release testing was performed using a UV spectrophotometer (Shimadzu UV-1700 spectrophotometer) with quartz cells, 1.0 cm light path. The procedure included the following.

The percutaneous permeation of topical and transdermal applied drugs was measured using a vertical diffusion cell (i.e. Franz diffusion cell). In this procedure porcine skin was used as a biological membrane. This procedure can be modified and adapted for similar biological membranes or equivalents.

Equipment and Materials

Vertical Diffusion Cell: 3×-PermaGear standard unjacketed Franz diffusion cell with clamp and stirbar: 9 mm:5 mL volume 0.64 square cm area.

Receptor Medium: The medium for the analysis can be determined by the biological conditions attempting to be replicated. To replicate standard biological conditions PBS, pH 7.4 was used as the receptor medium.

Membrane: Fresh porcine skin was cut into approximately 2.5×2.5 cm squares and frozen at −20 C in individually sealed packages until needed.

Procedure

Porcine skin samples were removed from −20 C and placed in a beaker filled with enough PBS to completely submerge all samples. The beaker was covered and placed in an incubator at 32 C for thirty minutes. Franz cells were prepared with the receptor cell containing 5 mL of PBS, pH 7.4, and pre-heated in the incubator for thirty minutes.

Franz cells were prepared using the porcine skin samples. The formulation being tested was added to the donor chamber of the photometer directly onto the skin via micropipetter.

The Franz cells were placed in the incubator on a stir plate with magnetic stir bar rotating at a moderate speed. Aliquotes (200 µL) of receptor solution were taken via the sampling port at specific time intervals (e.g. 0.5, 1, 1.5, 2, 3, 4, 5, 6 hrs) using a thin plastic pipette. Cells were refilled after each aliquote was taken by adding the same volume of pre-heated receptor medium. Samples were stored in microcentrifuge tubes at −20 C until analysis. Samples were analyzed using a Shimadzu UV-1700 Spectrophotometer. Data from 6 sets of samples may be collected and analyzed.

Results

The results in FIG. 2 are percent synephrine permeation as a function of time of the analyte through the porcine skin.

Example 8—Stability Data for Synephrine Compositions

Synephrine compositions were tested for stability over time. The composition of formula 01, containing 37% synephrine and PEG-6 caprylic/capric glycerides, was tested for stability. The incubator temperature was set to 40 degrees Celsius and relative humidity was set to 75%. Color, odor, pH, and specific gravity were recorded. Analytical assay testing was performed on the samples. The experimental conditions and results for certain characteristics measured over two months are shown in FIG. 3. FIG. 4 reports the results of testing for the presence of microbes over the same period of time. The data in FIGS. 3 and 4 shows that the composition is stable.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

All patents and other publications, including literature references, issued patents, published patent applications, and co-pending patent applications, cited throughout this application are expressly incorporated herein by reference in their entireties.

What is claimed is:

1. A composition comprising water, synephrine hydrochloride (HCl), pegylated caprylic/capric glycerides, and sodium metabisulfite and/or butylated hydroxytoluene, wherein synephrine HCl is present in an amount within a range from about 25% to about 40% by weight, wherein the sodium metabisulfite and/or the butylated hydroxytoluene reduces oxidation of the synephrine HCl, and the composition exhibits an absence of *Pseudomonas*, *Staphylococcus aureus*, *Escherichia coli*, Coliform, *Salmonella*, and *Shigella* microorganisms at 2 months of storage under the conditions of 40 degrees Celsius and 75% Relative Humidity.

2. The composition of claim 1, wherein the composition further comprises propanediol, phenoxyethanol, sodium metabisulfite, panthenol, niacinamide, ethylhexylgylcerin, and one or more preservative.

3. The composition of claim 2, wherein the composition further comprises a fragrance.

4. The composition of claim 1, wherein the composition comprises about 30% to about 50% by weight of water and about 5% to about 30% by weight of PEG-6 caprylic/capric glycerides.

5. The composition of claim 1, wherein the composition comprises about 40% to about 55% by weight of water, about 30% to about 40% by weight of synephrine HCl, and about 8% to about 12% by weight of PEG-6 caprylic/capric glycerides.

6. The composition of claim 1, wherein the composition comprises about 20% to about 50% by weight of water, about 5% to about 15% by weight of PEG-6 caprylic/capric glycerides, about 1% to about 5% by weight of propanediol, about 0.4% to about 3% by weight of phenoxyethanol and ethylhexylglycerin, about 0.1% to about 0.5% by weight of sodium metabisulfite, about 0.02% to about 0.5% by weight of panthenol, about 0.02% to about 1.0% by weight of niacinamide, and one or more preservatives.

7. The composition of claim 6, wherein the composition further comprises about 0.1% to about 2% by weight of a fragrance.

8. The composition of claim 6, wherein the composition comprises about 30% to about 35% by weight of water, about 28% to about 32% by weight of bitter orange extract, about 13% to about 15% by weight of glycolic acid, about 8% to about 12% by weight of PEG-6 caprylic/capric glycerides, about 6% to about 9% by weight of hydrochloric acid, about 2% to about 4% by weight of propanediol, about 0.7% to about 1.1% by weight of phenoxyethanol, about 0.2% to about 0.4% by weight of sodium metabisulfite, about 0.05% to about 0.15% by weight of panthenol, about 0.05% to about 0.15% by weight of niacinamide, about 0.07% to about 0.11% ethylhexylgylcerin, about 0.05% to about 0.15% by weight of butylated hydroxytoluene, and about 0.05% to about 0.15% by weight of tetrasodium EDTA.

9. The composition of claim 1, wherein the composition comprises about 20% to about 50% by weight of water, about 30% to about 60% by weight of synephrine HCl, and about 3% to about 20% by weight of PEG-6 caprylic/capric glycerides.

10. The composition of claim 1, wherein the composition further comprises R-(−)-synephrine.

11. The composition of claim 10, wherein the composition comprises about 20% to about 50% by weight of water, about 40% to about 70% by weight of synephrine HCl or R-(−)-synephrine, and about 5% to about 60% by weight of pegylated caprylic/capric glycerides.

12. The composition of claim 1, wherein the composition comprises about 20% to about 50% by weight of water, about 35% to about 64% by weight of synephrine HCl as determined by the equivalent mass of free base synephrine, and about 8% to about 20% by weight of PEG-6 caprylic/capric glycerides.

13. The composition of claim 1, further comprising a moisturizer.

14. The composition of claim 1, further comprising a surfactant and/or an emulsifier.

15. A composition comprising water, at least 30% w/w synephrine HCl, a penetration enhancer, and sodium metabisulfite and/or butylated hydroxytoluene, wherein the sodium metabisulfite and/or the butylated hydroxytoluene reduces oxidation of the synephrine HCl, and the composition exhibits an absence of *Pseudomonas, Staphylococcus aureus, Escherichia coli,* Coliform, *Salmonella,* and *Shigella* microorganisms at 2 months of storage under the conditions of 40 degrees Celsius and 75% Relative Humidity.

16. The stable aqueous composition of claim 15, wherein the penetration enhancer is caprylic/capric glycerides.

17. The stable aqueous composition of claim 16, wherein the composition comprises about 30% to about 50% by weight of water, about 25% to about 40% by weight of synephrine HCl, and about 5% to about 30% by weight of caprylic/capric glycerides.

* * * * *